(12) United States Patent
Caizza et al.

(10) Patent No.: US 7,972,303 B2
(45) Date of Patent: *Jul. 5, 2011

(54) SYRINGE WITH DISABLING MECHANISM

(75) Inventors: Richard Caizza, Vernon, NJ (US);
Robert B. Odell, Franklin Lakes, NJ (US); Brian H. Wayman, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 176 days.

This patent is subject to a terminal disclaimer.

(21) Appl. No.: 12/137,854

(22) Filed: Jun. 12, 2008

(65) Prior Publication Data

US 2009/0076450 A1 Mar. 19, 2009

Related U.S. Application Data

(60) Provisional application No. 60/943,397, filed on Jun. 12, 2007.

(51) Int. Cl.
*A61M 5/00* (2006.01)
(52) U.S. Cl. .................................................. 604/110
(58) Field of Classification Search .................. 604/110
See application file for complete search history.

(56) References Cited

U.S. PATENT DOCUMENTS

| | | | | |
|---|---|---|---|---|
| 4,367,738 A | * | 1/1983 | Legendre et al. | 604/110 |
| 4,915,692 A | * | 4/1990 | Verlier | 604/110 |
| 4,973,310 A | | 11/1990 | Kosinski | |
| 5,047,017 A | | 9/1991 | Koska | |
| 5,053,010 A | | 10/1991 | McGary et al. | |
| 5,106,372 A | | 4/1992 | Ranford | |
| 5,114,405 A | | 5/1992 | Winter | |
| 5,116,320 A | | 5/1992 | Lo Duca | |
| 5,188,616 A | * | 2/1993 | Nadal | 604/218 |
| 5,211,629 A | | 5/1993 | Pressley et al. | |
| 5,269,760 A | | 12/1993 | Bina | |
| 5,370,620 A | | 12/1994 | Shonfeld | |

(Continued)

FOREIGN PATENT DOCUMENTS

BE 1001579 A4 12/1989

(Continued)

OTHER PUBLICATIONS

PCT International Search Report and Written Opinion for PCT/US2008/066705, dated Jan. 30, 2009, 20 pp.

(Continued)

*Primary Examiner* — Nicholas D Lucchesi
*Assistant Examiner* — Jason Flick
(74) *Attorney, Agent, or Firm* — Jeanne P. Lukasavage; Diehl Servilla LLC

(57) ABSTRACT

Syringe assemblies having a passive disabling system to prevent reuse are provided. In one embodiment, the passive disabling system activates after completion of an injection cycle. An exemplary syringe assembly incorporates a stopper and plunger rod attached in a manner to prevent users from disassembling the syringe prior to completion of the injection cycle. The barrel may also include an annular extension or collar that extends from the proximal end of the barrel. In a specific configuration, the annular extension at least partially envelopes a portion of the thumb press to prevent the user from accessing the thumb press and moving the plunger rod in a proximal direction Syringe assemblies of one or more embodiments also include visual indicators or markers indicating whether a syringe assembly is used or the plunger rod is locked within the barrel.

38 Claims, 18 Drawing Sheets

U.S. PATENT DOCUMENTS

| | | | |
|---|---|---|---|
| 5,531,693 A | 7/1996 | Vounatsos | |
| 5,989,219 A | 11/1999 | Villas et al. | |
| 6,090,077 A | 7/2000 | Shaw | |
| 6,368,306 B1 | 4/2002 | Koska | |
| 6,599,269 B1 | 7/2003 | Lewandowski et al. | |
| 7,387,615 B2 * | 6/2008 | Coelho et al. | 604/110 |
| 2004/0176722 A1 | 9/2004 | Capes et al. | |
| 2005/0027250 A1 | 2/2005 | Suresh et al. | |
| 2006/0052748 A1 | 3/2006 | Coelho et al. | |
| 2006/0173411 A1 | 8/2006 | Barere | |

FOREIGN PATENT DOCUMENTS

| | | |
|---|---|---|
| EP | 0340899 | 11/1989 |
| EP | 1106194 | 6/2001 |
| EP | 1106194 A1 * | 6/2001 |
| FR | 2 686 517 | 7/1993 |
| FR | 2689765 | 10/1993 |
| GB | 2197792 A * | 6/1988 |
| WO | WO 90/03818 | 4/1990 |
| WO | WO 9003818 A1 * | 4/1990 |
| WO | WO-03/037411 | 5/2003 |
| WO | WO 2004/033008 | 4/2004 |
| WO | WO-2004/045683 | 6/2004 |
| WO | WO-2008/154616 | 12/2008 |

OTHER PUBLICATIONS

"PCT International Search Report mailed Sep. 19, 2008 for International Application No. PCT/US2008/066655 filed Dec. 6, 2008," 7 pgs.

"PCT Written Opinion mailed Sep. 19, 2008 for International Application No. PCT/US2008/066655 filed Dec. 6, 2008," 6 pgs.

"Non-Final Office Action", U.S. Appl. No. 12/137,854, (Feb. 4, 2010), 13 pgs.

"PCT Search Report and Written Opinion", PCT/US08/82045, (May 6, 2009), 14 pgs.

"Non-Final Office Action", U.S. Appl. No. 12/262,836, (Feb. 4, 2010), 16 pgs.

"Non-Final Office Action", U.S. Appl. No. 12/137,732 Jul. 21, 2010, 23.

"Non-Final Office Action", U.S. Appl. No. 12/262,836 Jul. 22, 2010, 23.

"Final Office Action in U.S. Appl. No. 12/137,732, dated Dec. 22, 2010", 27 pgs.

"Final Office Action in U.S. Appl. No. 12/262,836, dated Dec. 27, 2010", 25 pgs.

* cited by examiner

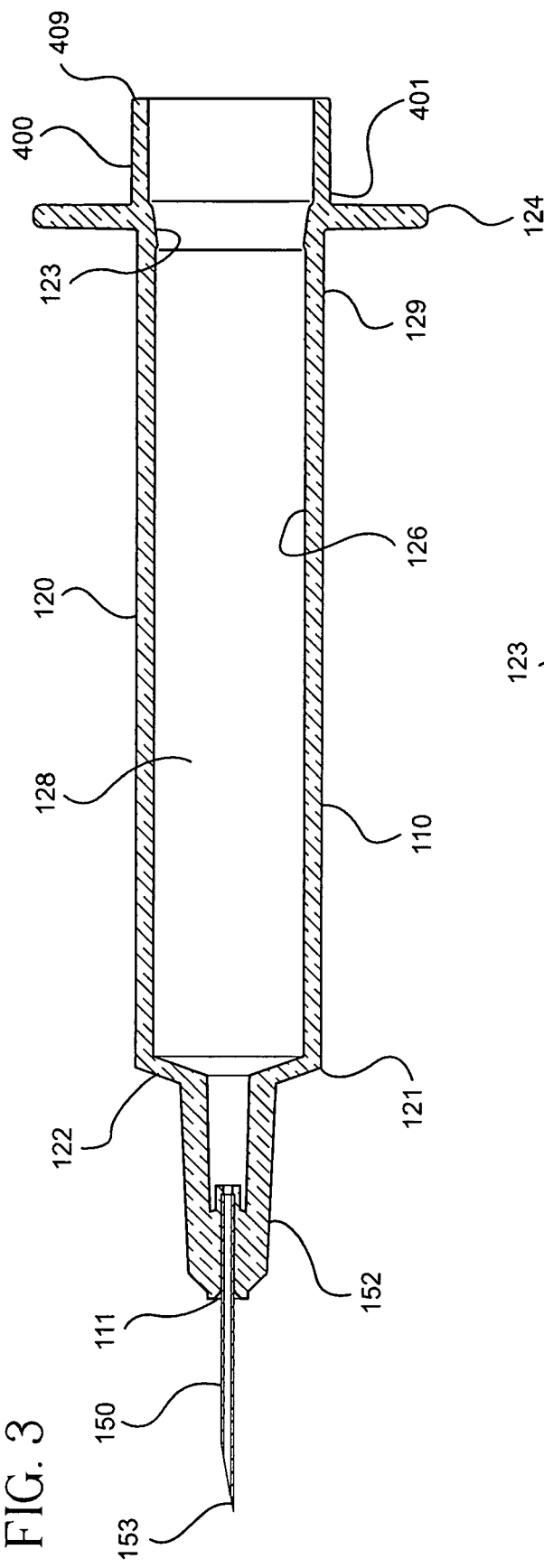
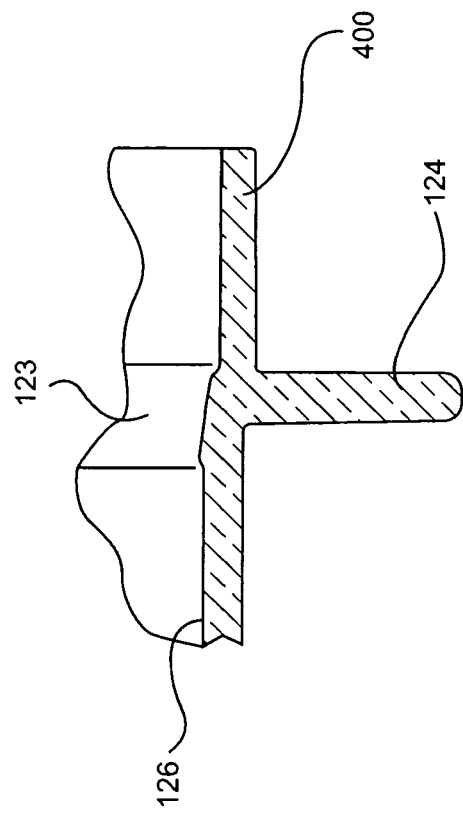
FIG. 3
FIG. 4

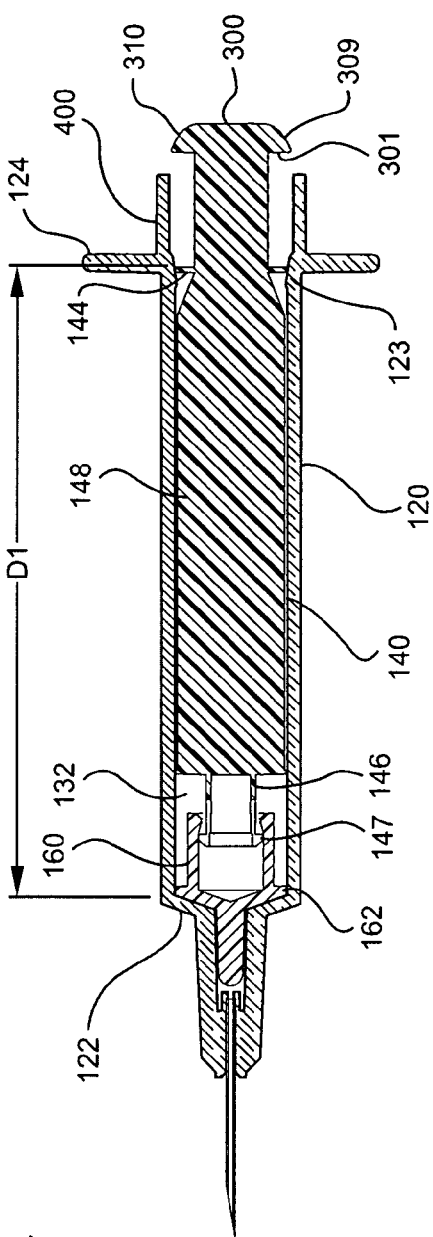
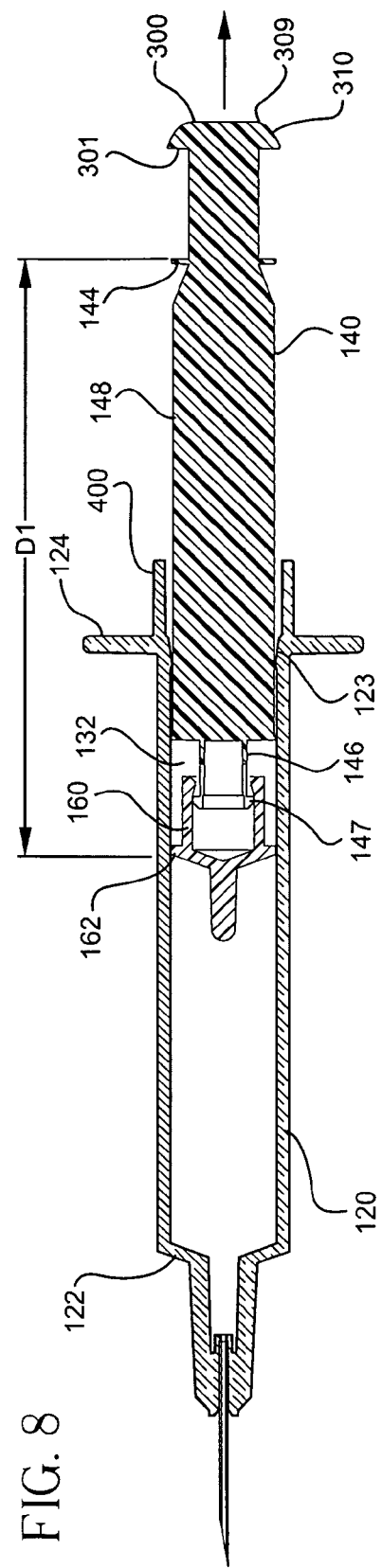

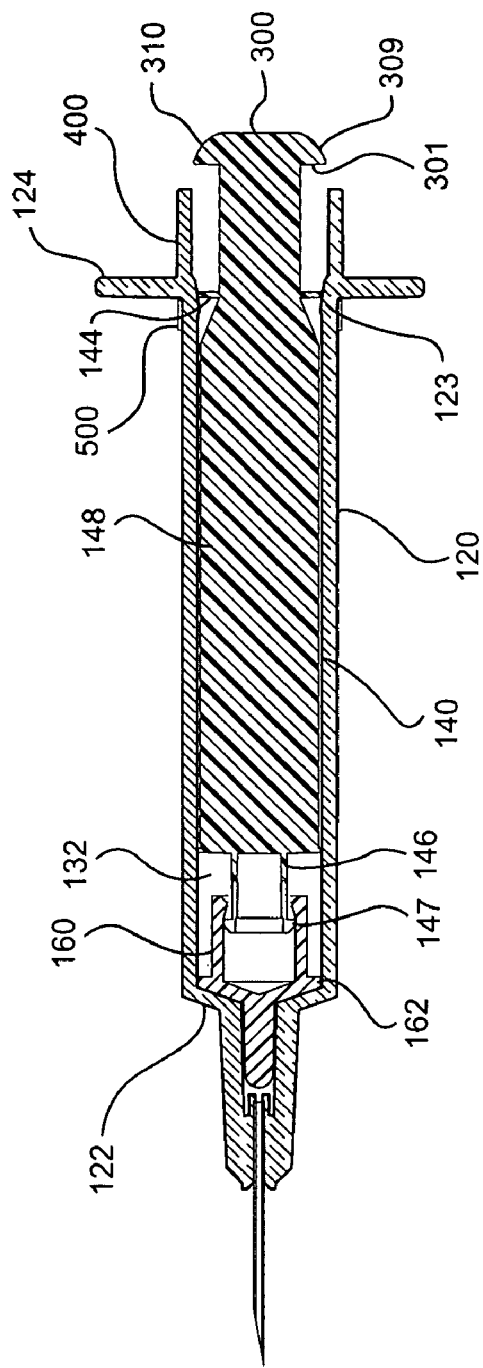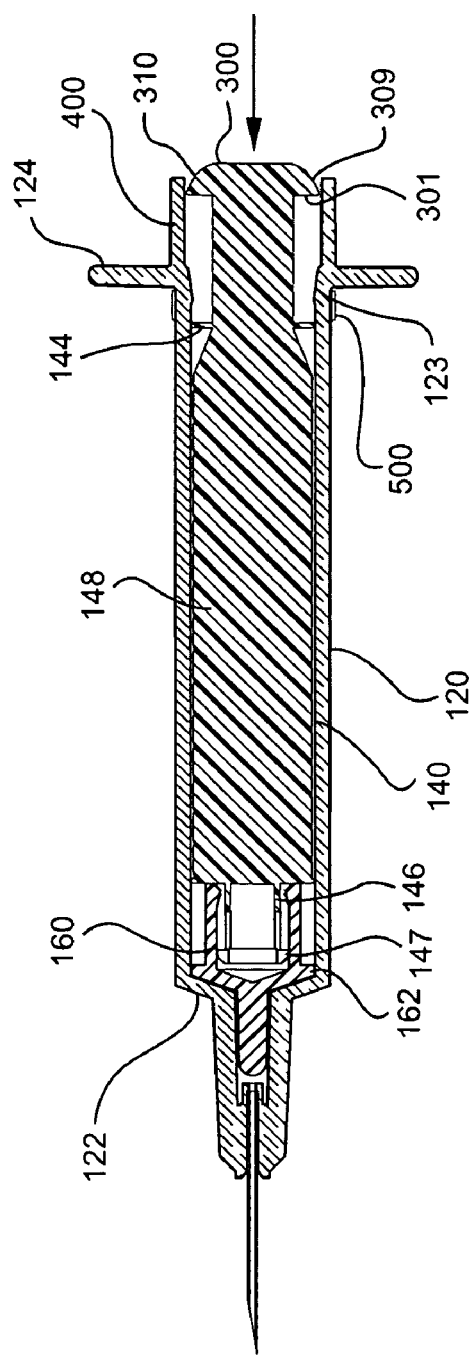

SYRINGE WITH DISABLING MECHANISM

CROSS-REFERENCE TO RELATED APPLICATIONS

This application claims the benefit of priority from U.S. Provisional Application No. 60/943,397, filed Jun. 12, 2007, the disclosures of which is hereby incorporated in its entirety by reference thereto.

TECHNICAL FIELD

The present invention relates to syringe assemblies having a passive disabling mechanism which restricts removal of the plunger rod after injection to prevent reuse, syringe assemblies wherein the stopper and plunger rod operate using relative motion to passively disable the syringe, syringe assemblies including a removeably connected stopper and plunger rod to prevent disassembly of the syringe prior to use and syringe assemblies including visual indication or markings to indicate use of the syringe or a disabled syringe.

BACKGROUND

Reuse of hypodermic syringe products without sterilization or sufficient sterilization is believed to perpetuate drug abuse and facilitate the transfer of contagious diseases. The reuse of syringes by intravenous drug users further exacerbates the transfer of contagious diseases because they comprise a high-risk group with respect to certain viruses such as the AIDS virus and hepatitis. A high risk of contamination also exists in countries with shortages of medical personnel and supplies.

A syringe which can be rendered inoperable after use presents a viable solution to these issues. Various syringes have been proposed and are commercially available that can be disabled by the user by taking active steps to disable the syringe. Single-use syringes that do not require the user to actively disable the syringe are also thought to offer a solution. It would be desirable to provide syringes that are automatically or passively disabled from reuse and can be manufactured in a cost-effective manner by, for example, utilizing fewer parts. Further, markings or other indicators which visually indicate whether a syringe has been used or is disabled would also be desirable.

SUMMARY

The present invention provides a passive disabling system for a syringe assembly, which activates after completion of an injection cycle. According to one or more embodiments of the invention, a syringe assembly incorporates a stopper and plunger rod attached in a manner to prevent users from disassembling the syringe prior to completion of the injection cycle. Accordingly, a means for preventing removal of a plunger rod from a syringe assembly is provided. A user of such a syringe can fill, inject and/or reconstitute medication.

In this disclosure, a convention is followed wherein the distal end of the device is the end closest to a patient and the proximal end of the device is the end away from the patient and closest to a practitioner.

A syringe assembly is provided which includes a barrel, an elongate plunger rod with a thumb press and stopper having respective structures and assembly which allow the user to passively restrict access or removal of the plunger rod from the barrel to prevent reuse of the syringe assembly. The barrel includes a distal end, an open proximal end, a cylindrical sidewall, which defines a chamber in which fluid may be held, and a distal wall. An opening in the distal wall permits fluid to flow from the chamber through the opening. The barrel may also include an annular extension or collar that extends from the proximal end of the barrel. The annular extension may have a diameter greater than the diameter of the plunger rod and the thumb press that is attached to the plunger rod. As will be more fully described herein, the annular extension provides a means for preventing removal of the plunger rod from the barrel after use. In one embodiment, the barrel includes a marker or indicator which indicates whether the syringe has been disabled or the plunger has been locked within the barrel.

In one or more embodiments, the sidewall of the barrel has a continuous diameter or first inner diameter. As used throughout this application, the term "diameter" is a measurement of the longest distance between the walls of the barrel having any cross-sectional shape. However, it will be appreciated that conventional syringes are typically cylindrical with a circular cross-sectional shape. In accordance with one or more embodiments of the present invention, the barrel includes a rib, locking rib or other such impediment suitable for restricting the proximal movement of the plunger rod, adjacent to its proximal end.

Embodiments of the present invention also include an extended plunger rod which has a proximal end, a distal end, and a main body between the proximal and distal end. In one or more embodiments, the plunger rod slides or otherwise moves proximally and distally within the chamber of the barrel. A thumb press is attached to the proximal end of the plunger. The thumb press includes a proximal end and a distal end and, in one or more embodiments, includes a diameter which can vary from the distal end to the proximal end. In a specific embodiment, the diameter of the thumb press decreases from the distal end to the proximal end.

In some embodiments, the distal end of the plunger includes a stopper-engaging portion having a distal and proximal end. The stopper-engaging portion of such embodiments provides a means for the stopper and plunger rod to move proximally and distally within the barrel. The stopper-engaging portion allows the stopper and plunger rod to move proximally and distally relative to each other. The stopper may move a pre-selected axial distance relative to the stopper-engaging portion of the plunger rod. In a specific embodiment, the stopper-engaging portion may include a rim at its distal end, a retainer or alternate means suitable for restraining the stopper. The stopper-engaging portion according to one or more embodiments may also include a visual indicator or a visual display that indicates use of the syringe or whether the syringe is disabled.

In an alternate embodiment, the stopper and the plunger rod are connected such that they move distally and proximally within the barrel in a fixed relationship. In such embodiments, when a user injects the entire contents of the syringe assembly, the stopper and plunger rod move distally within the plunger until the stopper reaches the distal wall and the thumb press moves within the barrel and/or the annular extension.

In accordance with one or more embodiments, the plunger rod further includes a means for locking the plunger rod in the barrel to prevent reuse of the syringe assembly when the syringe is fully injected or "bottomed." The means can have an outer diameter greater than the inner diameter of the barrel at the rib or the second inner diameter. As used herein, the term "bottomed" shall refer to the position of the syringe assembly wherein the stopper, while attached to the plunger rod, is in contact with the distal wall of the barrel and the plunger rod can no longer move in the distal direction. One or more embodiments of the present invention utilize a protrusion, or annular protrusion that extends radially from the plunger rod. In some embodiments, the protrusion is located between the thumb press and the main body, as an example of a means for locking the plunger rod in the barrel. According to an embodiment of the invention, the protrusion is integrally molded to the plunger rod.

In a specific embodiment, the protrusion can have an outer diameter greater than the second inner diameter. In this specific configuration, once the protrusion distally moves past the rib and into the barrel, it becomes locked by the rib, thereby preventing proximal movement of the plunger rod. The protrusion can be tapered or otherwise shaped in such a manner such that it may move in the distal direction past the rib more easily.

The stopper has a proximal end and a distal end, and the stopper is attached the stopper-engaging portion of the plunger rod. The stopper may further comprise a stopper body or stopper boss at the proximal end of the stopper. A peripheral lip may be included at the proximal end of the stopper body. A frangible connection may be provided to connect the stopper to the plunger rod, which may connect the stopper and the peripheral lip.

In embodiments where the stopper moves distally and proximally relative to the stopper-engaging portion of the plunger rod, the stopper-engaging portion of the plunger rod and the stopper may be connected in a manner such that when the user applies a force in the proximal direction for aspiration or filling the syringe, the stopper remains stationary until plunger rod moves in the proximal direction the length of the pre-selected axial distance. In one embodiment, when a user continues to aspirate or fill the syringe assembly, the stopper begins to move in the proximal direction in tandem with the plunger rod, after the plunger rod has traveled the pre-selected axial distance in the proximal direction. An optional visual indicator or display disposed on the stopper-engaging portion of the plunger rod is visible when the user fills the syringe assembly.

In one or more embodiments in which the stopper can move relative to the stopper-engaging portion of the plunger rod, when a user injects the contents of the syringe assembly, the attachment of the stopper and the stopper-engaging portion allows the plunger rod to move distally for a length of the pre-selected axial distance, while the stopper remains stationary. After the plunger rod travels distally for the length of the pre-selected axial distance, the stopper begins to move distally with the plunger rod. During such distal movement, where a visual indicator or display is utilized, the visual indicator or display disposed on the stopper-engaging portion of the plunger rod is no longer visible. Where a visual marker is utilized, the visual marker disposed on the barrel continues to be visible, even after the plunger rod is locked. As will be more fully described herein, the marker provides an alternative means of indicating the syringe has been disabled. For example, in one such alternative means, the plunger rod may optionally include a visual alignment marker which moves from being proximally adjacent to the visual marker to being distally adjacent to the visual marker when the syringe assembly is disabled. In a specific embodiment, the visual alignment marker can include the protrusion.

In a specific configuration, the total length of the plunger rod is decreased by pre-selected axial distance when the stopper and plunger rod move together in the distal direction during injection of the contents of the syringe assembly. As such, the stopper and stopper-engaging portion of the syringe assembly are attached in a manner such that when a user has fully completed the injection cycle and the stopper is in contact with the distal wall of the barrel, the thumb press moves distally into or nestably engages with the annular extension or collar at the proximal end of the barrel. The annular extension or collar is configured to partially envelope a portion of the thumb press, thereby preventing the user from accessing the thumb press and pulling the plunger rod out of the barrel. In a specific embodiment, the annular extension or collar is shaped to provide a nesting area for the thumb press or to fully envelope the thumb press when the stopper is in contact with the distal wall of the barrel. In a more specific embodiment, the annular extension and thumb press include locking features, such as a detent and cooperating tab or retaining ring, which are configured to lock the thumb press at the proximal end of the barrel when the thumb press moves distally into the annular extension. Once the total length of the plunger rod is decreased by the pre-selected axial distance and the thumb press has moved into the annular extension, the optional visual indicator or display on the stopper-engaging portion of the plunger rod is no longer visible, indicating the syringe has been disabled.

In embodiments that utilize a means for locking the plunger rod in the barrel, the distal movement of the stopper and plunger rod allows the protrusion to move past the rib into the locked position. In specific embodiments, the relative movement of the stopper and the stopper-engaging portion also allows the protrusion to move distally past the rib into the locked position, when the syringe assembly is bottomed. In the embodiments that utilize a means for locking the plunger rod in the barrel, once the protrusion advances past the rib of the barrel, it locks the plunger rod within the barrel and prevents the user from reusing the syringe assembly or otherwise pulling the plunger rod out of the barrel. Once the plunger rod is locked within the barrel, the optional visual indicator or display on the stopper-engaging portion of the plunger rod is no longer visible, indicating the syringe has been disabled. When a visual marker disposed on the barrel is utilized, the visual marker remains visible and indicates when the plunger rod has been locked within the barrel.

In one or more embodiments, the syringe assembly may include one or more frangible portions of the plunger rod, which break when a user attempts to move the plunger rod in a proximal direction after the protrusion has advanced past the rib of the barrel. Other suitable means may be utilized for separating a portion of the plunger rod from the main body when the user applies sufficient proximal force to the plunger rod or otherwise attempts to reuse the syringe assembly after it is bottomed.

In accordance with one embodiment of the invention, the stopper and the stopper-engaging portion are attached in such a manner such that when a user attempts to disassemble the syringe assembly prior to aspiration, injection or bottoming, the stopper-engaging portion disengages from the stopper, leaving the stopper inside the barrel and allowing the separated plunger rod to be removed. In some embodiments, inner diameter of the barrel at the rib, or the second inner diameter, is less than the outer diameter of the stopper, and thereby prevents the stopper from moving proximally past the rib and causes the stopper-engaging portion to detach from the stopper, leaving the stopper inside the barrel. An optional frangible connection of the stopper breaks when a user attempts to disassemble the syringe assembly by applying a continuous force in the proximal direction to the plunger rod prior to aspiration, injection or bottoming.

BRIEF DESCRIPTION OF THE DRAWINGS

FIG. 3 shows a cross-sectional view of the barrel shown in FIG. 2 taken along line 3-3;

FIG. 4 is an enlarged view of a portion of the barrel shown in FIG. 3;

FIG. 7 is a cross-sectional view taken along line 7-7 of FIG. 1;

FIG. 8 is an illustration of FIG. 7 showing the plunger rod being moved in the proximal direction;

FIG. 16 is a cross-sectional view taken along line 16-16;

FIG. 17 is an illustration of FIG. 16 showing the plunger rod in a locked position in the syringe barrel;

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

One aspect of the present invention provides for a syringe assembly including a barrel, plunger rod and stopper having individual features and construction which allow the user to passively lock the plunger rod within the barrel to prevent reuse of the syringe assembly.

Figure 1:
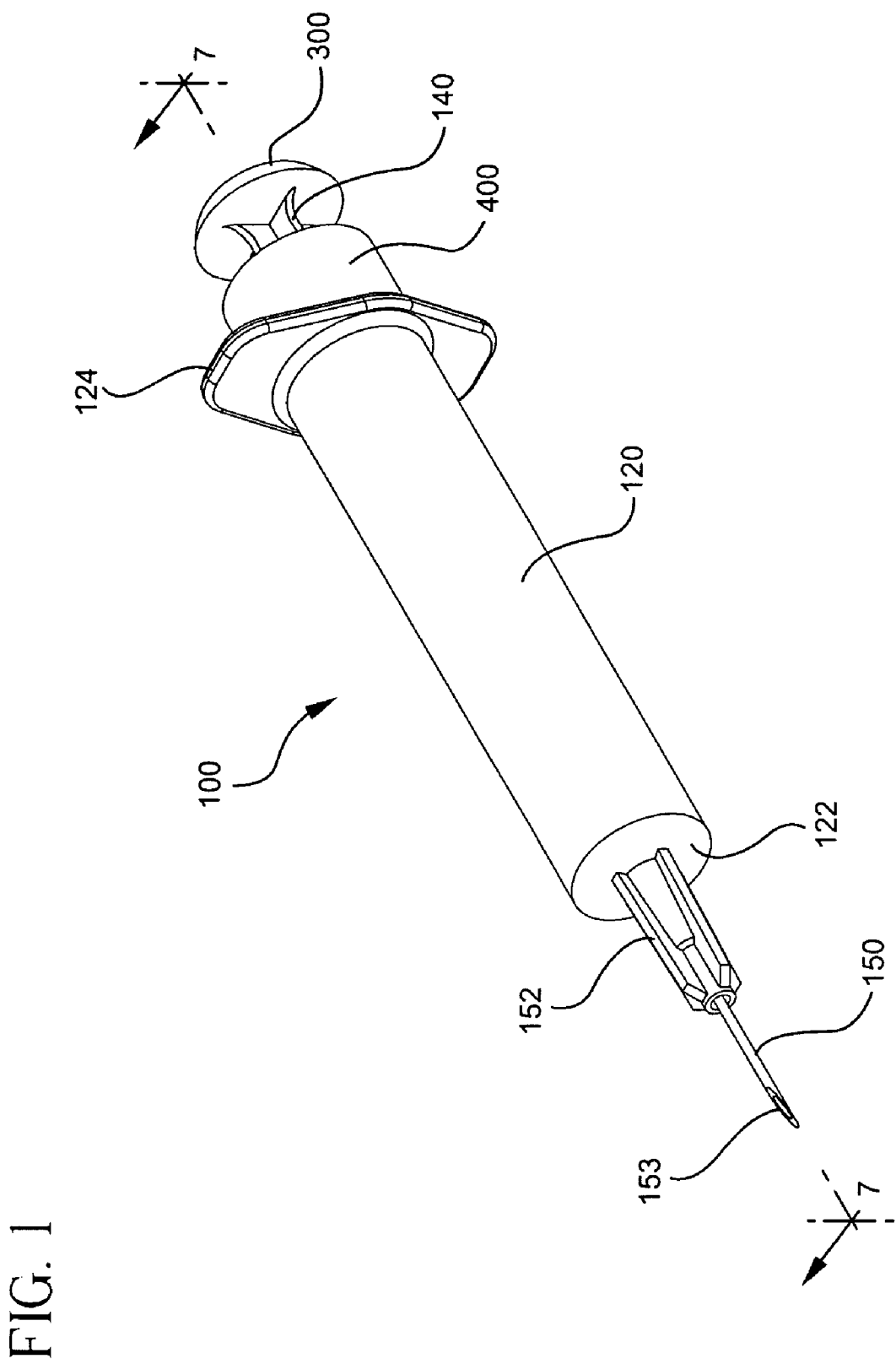
FIG. 1 illustrates a perspective view of a syringe assembly according to an embodiment of the invention shown.
Figure 2:
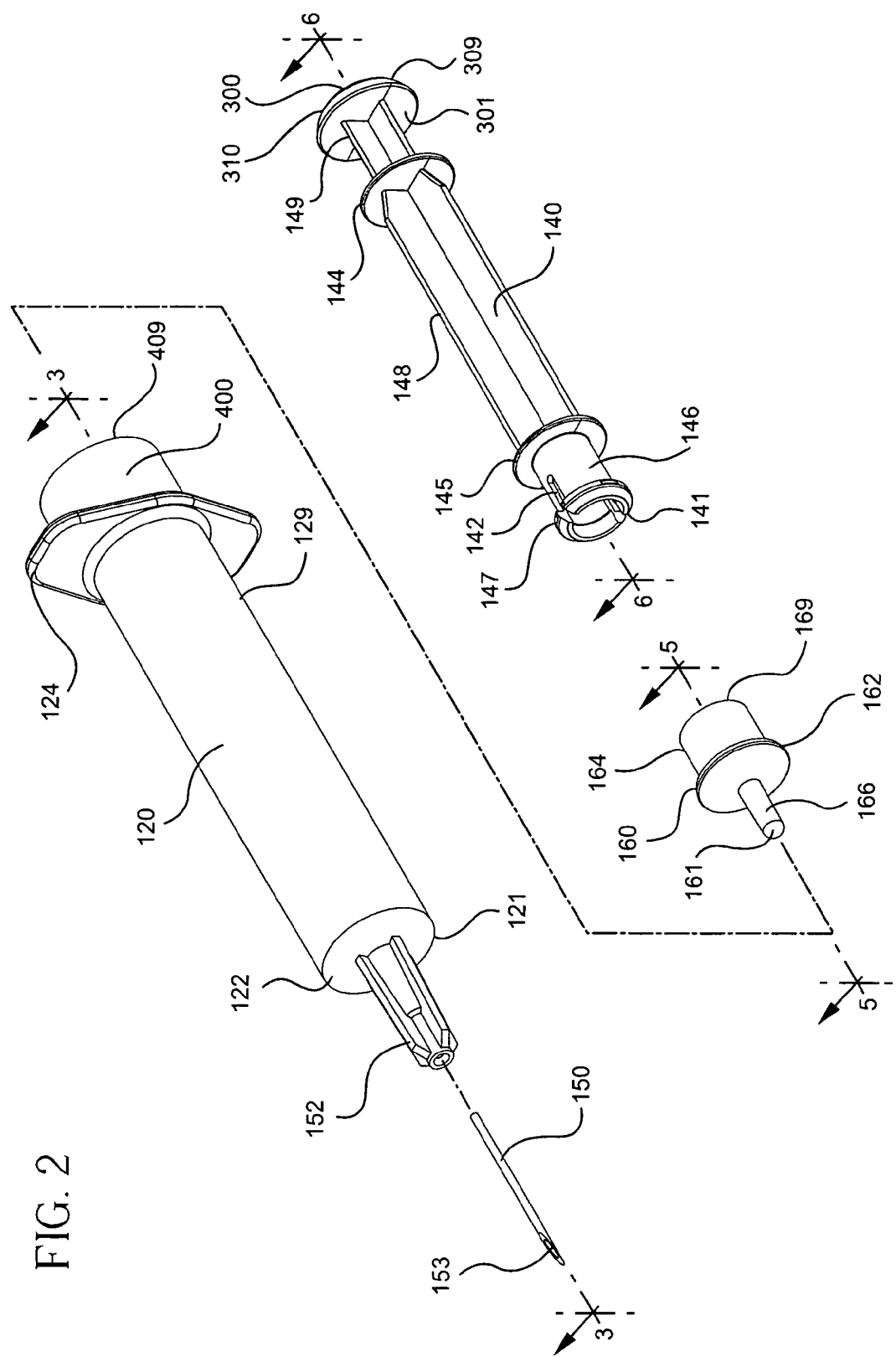
FIG. 2 illustrates a disassembled perspective view of the syringe assembly shown in FIG. 1.

FIG. 1 shows a syringe assembly 100 according to one or more embodiments. As shown in FIG. 2, the syringe assembly includes a barrel 120, a plunger rod 140 and a stopper 160, arranged such that the proximal end 169 of stopper is attached to the distal end 141 of the plunger rod. The connected stopper 160 and plunger rod 140 are inserted into the proximal end 129 of the barrel 120.

As best shown in the FIG. 3, the barrel 120 has a cylindrical sidewall 110 with an interior surface 126 that defines a chamber 128. In one embodiment, the chamber 128 holds the contents of the syringe assembly which may include medication in powdered or fluid form. The barrel 120 is shown as having an open proximal end 129, a distal end 121, and a distal wall 122. The distal wall 122 has an opening 111 in fluid communication with the chamber 128.

The sidewall 110 of the barrel 120 defines a chamber having a continuous inner diameter along the longitudinal axis of the syringe. Alternatively, the barrel can include a sidewall has an inner diameter, which decreases linearly from the proximal end to the distal end. It is to be understood that the configuration shown is merely exemplary, and the components can be different in shape and size than shown. For example, the barrel can have an exterior prism shape, while retaining a cylindrical interior shape. Alternatively, both the exterior and interior surfaces of the barrel can have non-circular cross-sectional shapes.

The syringe barrel 120 is shown as having a peripheral flange 124 attached at the proximal end 129 of the barrel 120. The barrel 120 further includes a needle cannula 150, having a lumen 153 attached to the opening 111 in the distal wall 122 of the barrel 120. As is known in the art, attachment means 152 is provided for attaching the needle cannula 150 to the distal wall 122. The assembly 100 may also include a protective cap over the needle cannula (not shown).

Referring to FIG. 3, the proximal end of the barrel 129 includes an annular extension or collar 400. The annular extension 400 includes a proximal end 409 and a distal end 401. As will be more fully described herein, the annular extension 400 can have a diameter greater than the diameter of the thumb press 300 and, in one or more embodiments, the annular extension 400 can also have a length that would allow it to envelope or cover the thumb press 300 after a full injection cycle.

As shown more clearly in FIG. 3, the barrel 120 further includes a rib 123 adjacent its proximal end 129. The rib 123 is distally adjacent to the annular extension 400. In one or more embodiments, the rib 123 can be formed on the interior wall of the annular extension (not shown), and, in such embodiments, to provide a means for locking the plunger rod disposed on the plunger rod such that it advances distally past the rib 123 when the stopper 160 is in contact with the distal wall 122 of the syringe. In a specific embodiment, a plurality of ribs is disposed on the interior surface 126 of the barrel. In a more specific embodiment, one rib is distally adjacent to the annular extension and a second rib is formed on the interior wall of the annular extension. The inner diameter of the barrel at the location of the rib 123 is smaller than the inner diameter of the barrel 120 at other locations along the length of the barrel. Instead of a continuous rib 123, one or more optional tabs or detents can be used to create a region of the barrel having a diameter smaller than the inner diameter of the barrel 120. Thus, the plunger rod can be retained in the barrel by such tabs that are co-radial with tabs or detents on the plunger rod. In a specific embodiment, the rib can include a ring formed along entire circumference of the interior surface 126 or a portion of the interior surface 126 of the inner diameter of the barrel 120 (not shown). In one or more embodiments, the barrel 120 also may include a diameter transition region proximally adjacent to the rib 123 (not shown). In such a configuration, the inner diameter of the barrel at the diameter transition region increases from the distal end 121 to the proximal end 129 of the barrel 120. The barrel may also include an increased diameter region proximally adjacent to the diameter transition region (not shown). In such a configuration, the increased diameter region has a greater inner diameter than the inner diameter of the barrel of the entire diameter transition region.

The barrel may be made of plastic, glass or other suitable material. The barrel further includes optional dosage measurement indicia (not shown).

Figure 5:
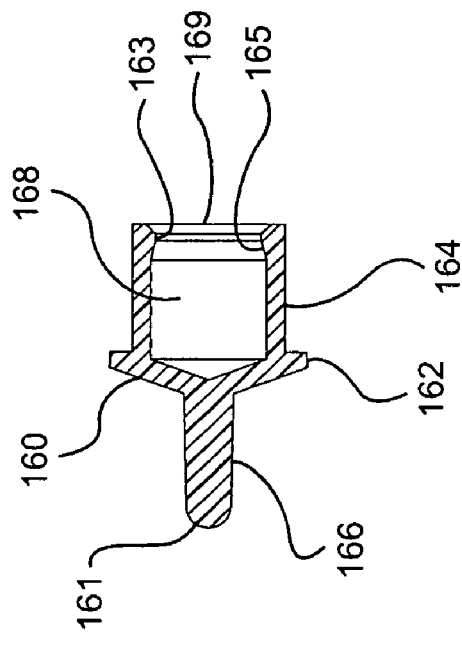
FIG. 5 is a cross-sectional view of the stopper shown in FIG. 2 taken along line 5-5.

Referring now to FIG. 5, the shown stopper 160 has a distal end 161, a proximal end 169, a stopper body 164 and a peripheral edge 162 which forms a seal with the interior surface 126 of the barrel. In one or more embodiments, the peripheral edge 162 of the stopper 160 has a larger diameter than the diameter of the interior surface of the rib 123. The stopper 160 shown in FIG. 5 includes an optional elongate tip 166 on its distal end 161 to facilitate reduction of the residual fluid and expulsion of fluid from the syringe barrel.

The stopper 160 is shown as further having a tapered portion 165 adjacent to the stopper body 164 at its proximal end 169. A neck 163 is adjacent to the tapered portion 165 at the proximal end 169 of the stopper 160. The stopper body 164 is shown as also including an interior recess 168, which allows the stopper 160 to connect to the plunger rod.

The stopper is typically made of plastic or other easily disposable and/or recyclable material. It may be desirable to incorporate natural or synthetic rubber in the stopper or use a natural or synthetic rubber seal with the stopper. It will be understood that the stopper may incorporate multiple seals.

Figure 6:
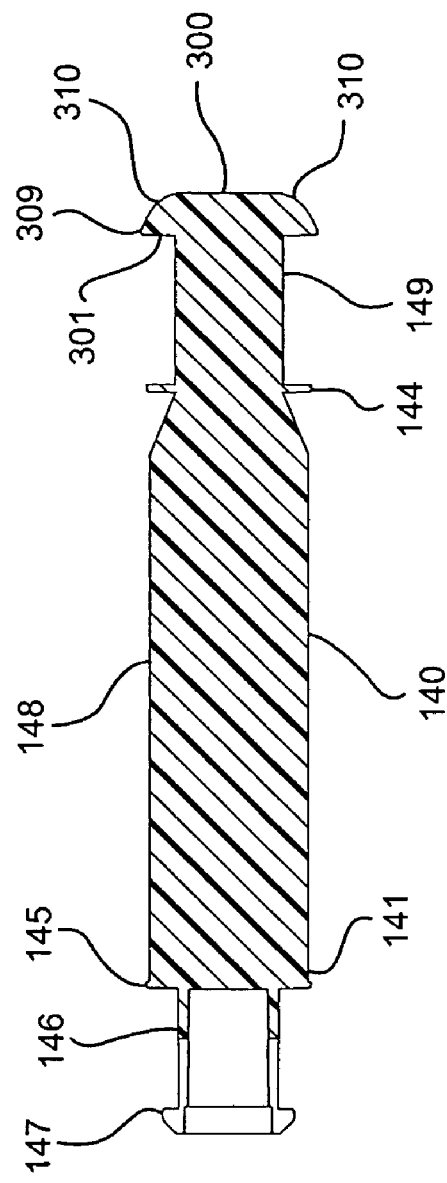
FIG. 6 is a cross-sectional view of the plunger rod shown in FIG. 2 taken along line 6-6.

Referring now to FIG. 6, the syringe assembly includes a plunger rod 140 having a proximal end 149, a distal end 141, and a main body 148 extending between the proximal end 149 and distal end 141. The distal end 141 of the plunger rod includes a stopper-engaging portion 146 which connects the stopper 160 to the plunger rod 140. A peripheral rim 147 may be provided to help retain the stopper 160 on the plunger rod 140. As with the rib of the barrel, detents or tabs can be used to retain the stopper 160 on the plunger rod 140. The stopper-engaging portion 146 may also include one or more notches 142 at the distal end 141 of the plunger rod.

The plunger rod 140 further includes a thumb press 300 at the proximal end 149 of the plunger rod 140. In the embodiment shown, the thumb press 300 further includes a distal end 301, a proximal end 309 and contoured portion 310 between the distal end and the proximal end. The contoured portion 310 includes a segment of the thumb press having a diameter that decreases from the distal end 301 to the proximal end 309 of the thumb press. In one or more embodiments, the proximal end of the thumb press 309 can have a flat surface or can be curved. In a specific embodiment, the thumb press can be contoured to fit within the barrel after a full injection cycle. In a more specific embodiment, the thumb press can be contoured to at least partially nest or fit within the annular extension disposed at the proximal end of the barrel. In an even more specific embodiment, the thumb press can includes a writeable surface and/or label.

Still referring to FIG. 6, the plunger rod 140 further includes a protrusion 144 shown as a protrusion 144 between the thumb press 300 and the main body 148. The outer diameter of the plunger rod at the protrusion 144 is greater than the inner diameter of the barrel 120 at the rib 123. In a specific embodiment of the invention, the protrusion 144 includes a tapered portion that facilitates distal movement of the protrusion past the rib 123 and into the barrel 120, as will become apparent in the subsequent discussion of operation of the syringe. In at least one embodiment, the syringe assembly is configured to allow the protrusion 144 to advance distally past the rib 123, to lock the plunger rod in the barrel when the user bottoms out the plunger rod in the barrel (as more clearly shown in FIGS. 10 and 11). The plunger rod 140 may also include a disc 145 disposed at the distal end 141 of the plunger rod. In one embodiment, the disc 145 is the means for locking the plunger rod within the barrel.

In the embodiment shown, the stopper 160 is permitted to move distally and proximally within the barrel when connected to the stopper-engaging portion 146 of the plunger rod 140. As will be understood better with the description of operation of the syringe assembly and with reference to FIG. 7, the stopper is capable of moving distally and proximally a pre-selected axial distance 132 relative to the stopper-engaging portion. In an alternate configuration, the stopper and plunger rod may be connected in a fixed relationship where the stopper is prevented from moving distally and proximally relative to the stopper-engaging portion or the plunger rod.

The plunger rod may be made of plastic or other suitable material. The protrusion may also be comprised of plastic or a harder material suitable for locking the plunger rod within the barrel. Similarly, the thumb press may be made of plastic or other suitable material. In a specific embodiment, the thumb press is made of a material which creates a slippery surface, which requires the user to be able to grasp a greater surface area to remove the plunger rod or to apply a force to the plunger rod in the proximal direction.

In FIG. 7, the barrel 120 holds the stopper 160 and plunger rod 140 in the chamber, wherein the stopper is bottomed, "parked" or is in contact with the distal wall 122 of the barrel 120. The peripheral edge of the stopper 162 forms a seal with the interior surface 126 of the barrel 120. In one embodiment, the stopper 160 is connected to the stopper-engaging portion 146 of the plunger rod 140. The stopper-engaging portion 146 is removeably held in the recess 168 of the stopper body 164 by the neck 163.

In the alternate configuration in which the stopper and plunger rod are connected in a fixed relationship, the stopper is not parked and is positioned within the barrel at a distance between the distal wall and the stopper. In this configuration, when the stopper is moved distally and is in contact with the distal wall, the thumb press is permitted to move within the barrel or annular extension. In one such specific embodiment, the syringe assembly is pre-filled with medication, with the stopper positioned at the proximal end of the barrel.

Referring to FIG. 7, a gap between stopper 160 and the distal end of the main body 148, before commencement of the injection cycle, defines the pre-selected axial distance 132. The thumb press remains outside the barrel 120 and the annular extension 400 because the combined length of the plunger rod 140 and stopper, along with the pre-selected axial distance 132, is greater than the length of the barrel 120 from the distal wall 122 to the proximal end of the annular extension 409. In the embodiment shown in FIG. 7, the protrusion 144 also remains on the proximal side of the rib 123 for this reason.

The distance between the protrusion 144 and the peripheral edge 162 of the stopper 160 defines a first distance, D1. In configurations that do not include a protrusion 144, D1 may be the distance from the peripheral edge of the stopper 160 to the proximal end 309 of the thumb press or any other fixed point on the plunger rod.

FIG. 8 illustrates the syringe assembly in use and specifically shows an aspiration or filling step, according to one or more embodiments of the present invention. When the user applies a force to the plunger rod 140 in the proximal direction shown by the arrow in FIG. 8, the plunger rod 140 and the stopper 160 move together in the proximal direction, while the stopper-engaging portion 146 is connected to the stopper 160 by the rim 147. In one or more embodiments, the gap defining the pre-selected axial distance 132 is maintained while the stopper 160 and plunger rod 140 move together in the proximal direction along the interior surface of the syringe barrel. The user terminates the application of proximal force on the plunger rod 140 once the desired amount of medicament is drawn into the syringe. During the aspiration step, the plunger rod and the stopper body move in the proximal direction together to draw medication into the syringe, while maintaining the first distance D1.

Figure 9:
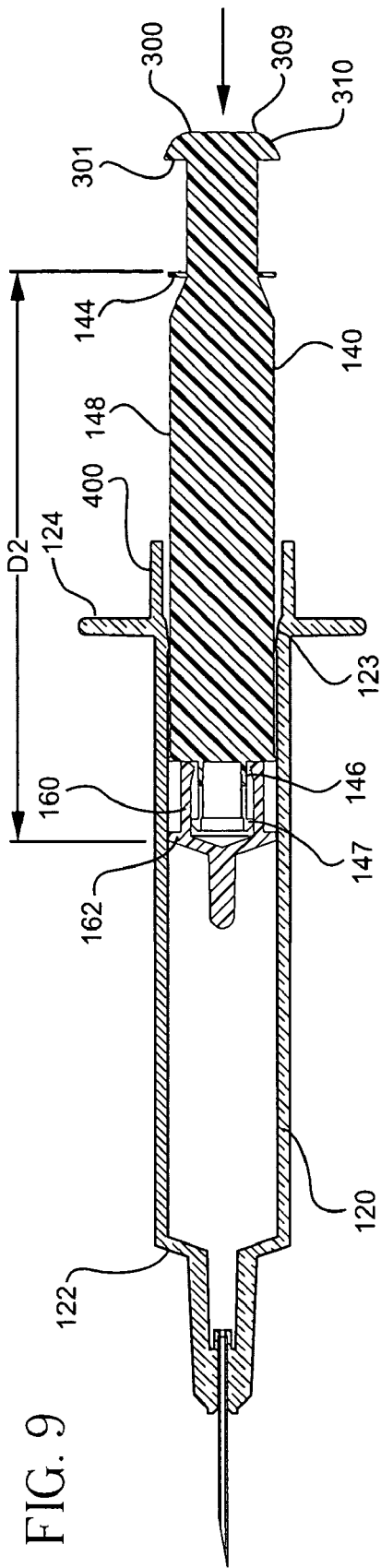
FIG. 9 is an illustration of FIG. 8 showing the plunger rod being moved in the distal direction.

FIG. 9 also shows the syringe assembly in use and specifically demonstrates application of distal force to the plunger rod during injection. In one embodiment, when the user applies a force in the distal direction to the plunger rod 140 as indicated by the arrow, the plunger rod 140 moves in a distal direction for the length of the gap defining the pre-selected axial distance 132 in FIG. 7, while the stopper 160 remains stationary. The stopper 160 remains stationary because the frictional force created by the peripheral edge 162 of the stopper on the interior surface 126 of the barrel is greater than the frictional force created by the stopper-engaging portion 146 entering the recess 168 of the stopper 160. Consistent with at least one embodiment, once the stopper-engaging portion has distally moved the length of the pre-selected axial distance 132 and is in contact with the proximal end of the recess 168, the stopper 160 and the plunger rod 140 begin to move in tandem in the distal direction. Further, the force applied by the user is greater than the friction between the peripheral edge 162 of the stopper 160 and the interior surface 126 of the barrel, and therefore the stopper 160 is forced to move in the distal direction with the plunger rod 140. In one embodiment, the user may inject a limited amount of the fluid aspirated or exert a limited force on the plunger rod in the distal direction to flush or expel some of the aspirated fluid, without locking the plunger rod, provided that the syringe assembly is not bottomed. However, as will be described further with respect to FIG. 10, a user may bottom the stopper against the distal wall of the syringe barrel, locking the plunger rod in the barrel.

When expelling the contents of the syringe, the plunger rod moves in a distal direction the length of the pre-selected axial distance 132 shown in FIG. 7 while the stopper body remains stationary, consequently closing the gap defining the pre-selected axial distance 132. After the contents of the syringe have been fully expelled, the distance between the protrusion 144 and the peripheral edge 162 defines a second distance, D2, wherein D2 is the difference between the first distance, D1, and the gap defining a pre-selected axial distance 132.

Figure 10:
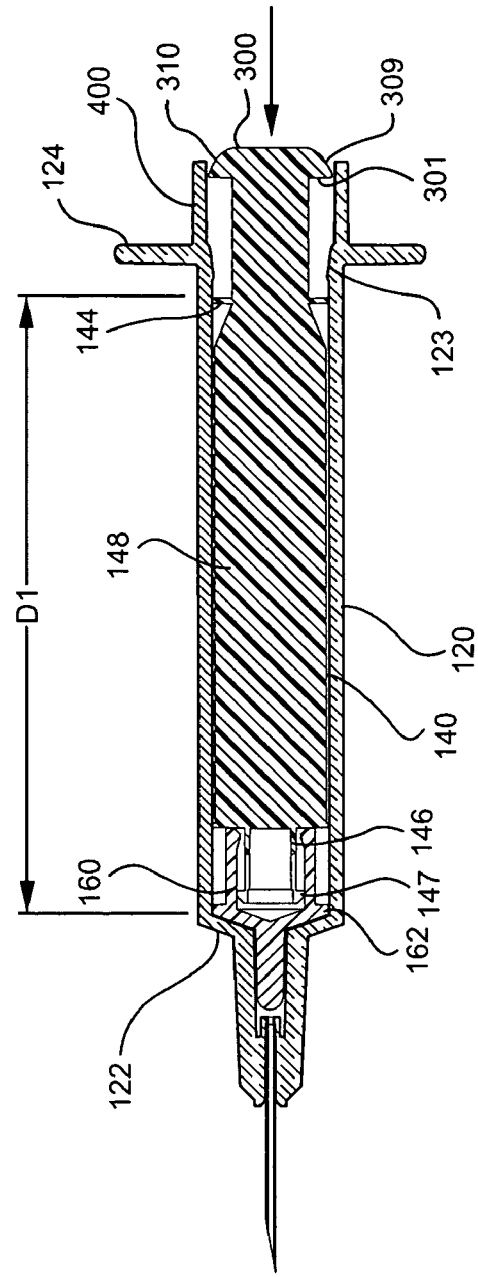
FIG. 10 is an illustration of FIG. 9 showing the plunger rod in a locked position in the syringe barrel.
Figure 11:
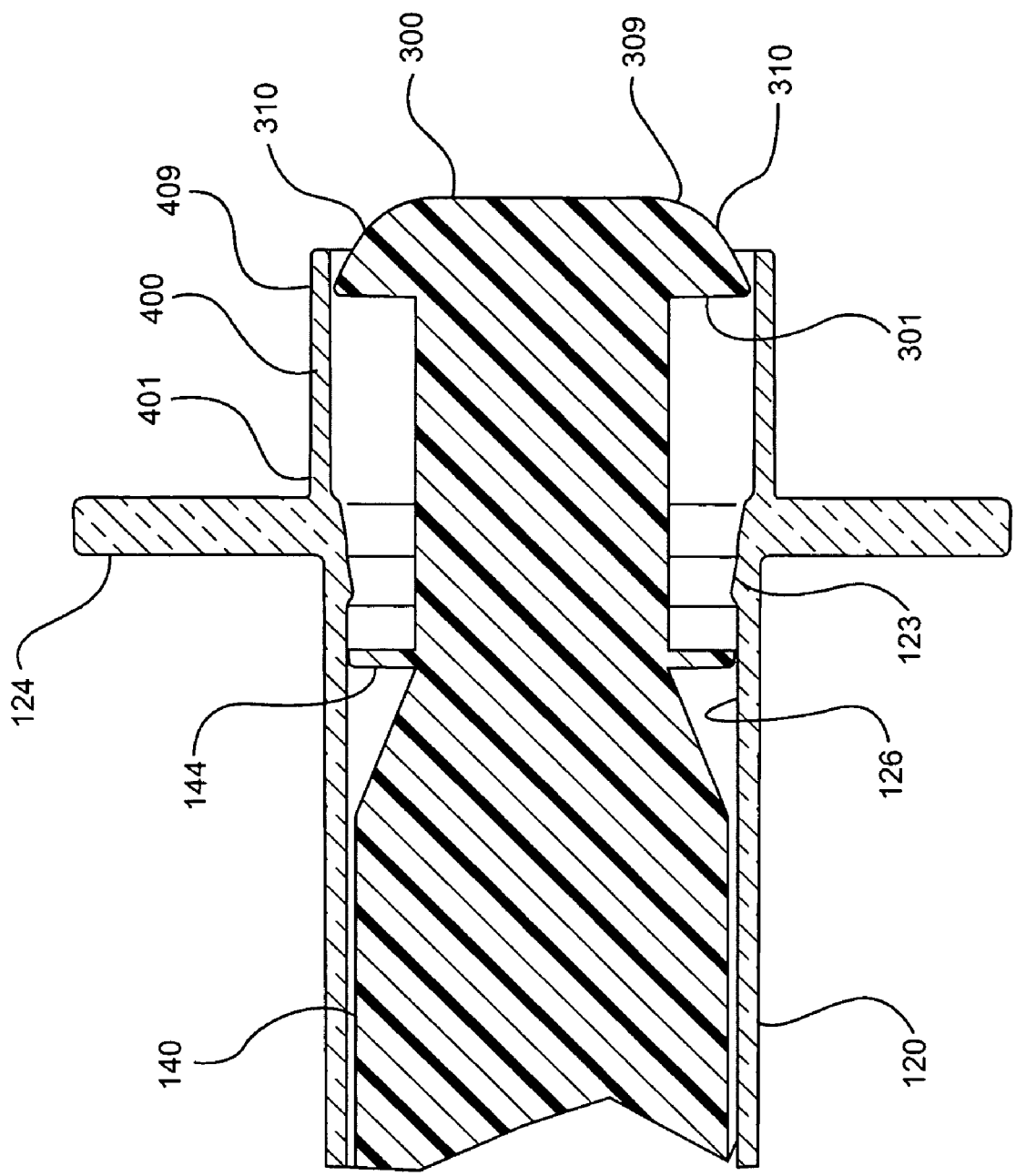
FIG. 11 is an enlarged view of a proximal portion of the assembly shown in FIG. 10.

FIG. 10 illustrates an embodiment of the syringe assembly after the plunger rod has been locked inside the barrel. In one or more embodiments, the entry of the stopper-engaging portion into the recess 168 of the stopper 160 (as also shown in FIG. 9) closes the gap defining the pre-selected axial distance 132, allowing the protrusion 144 to advance past the locking rib 123 (as more clearly shown in FIG. 11). The protrusion 144 has an outer diameter greater than the inner diameter of the barrel at the rib 123. Accordingly, in one or more embodiments, the rib 123 locks the protrusion 144 inside the barrel 120, and prevents proximal movement of the plunger rod 140. In the embodiment shown, the thumb press 300 is also allowed to advance distally into the annular extension 400. As more clearly shown in FIG. 11, the thumb press 300 advances distally into the annular extension 400 such that the annular extension covers a portion of the thumb press 300, leaving the remaining portion of the thumb press extending past the protrusion. In such embodiments, the thumb press can be made difficult to grasp by the use of the optional contoured portion 310.

In embodiments wherein the stopper is connected in a fixed relationship to the plunger rod, after the contents of the syringe have been fully expelled, the gap between the stopper and distal wall is closed, thereby permitting the thumb press to move within the barrel or annular extension and, where a rib and/or protrusion are utilized, permitting the protrusion to advance distally past the rib.

Figure 12:
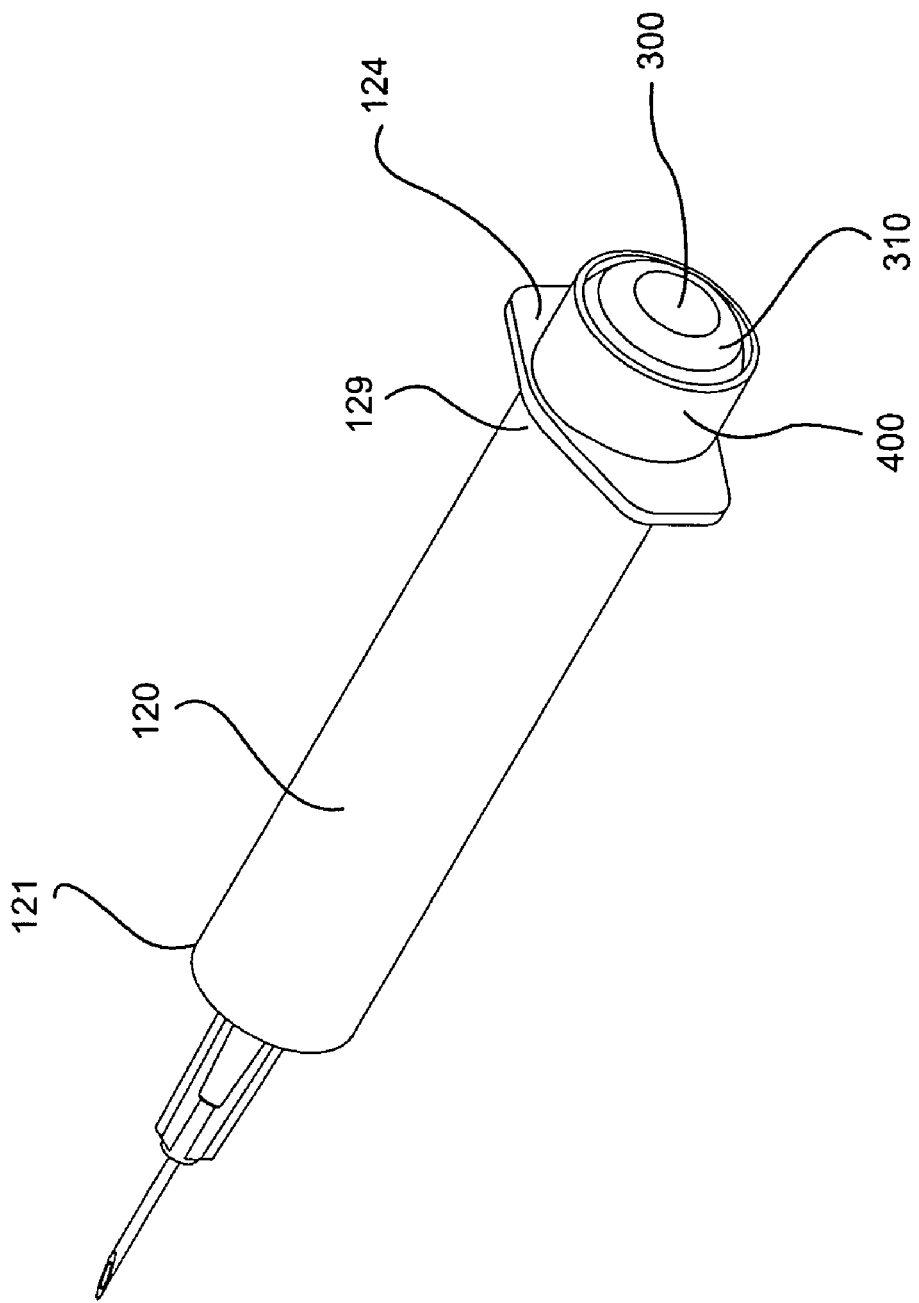
FIG. 12 illustrates a perspective view of FIG. 10.

According to the embodiment of FIG. 12, the annular extension 400 can cover the entire length of the thumb press 300, prohibiting access to the thumb press. In embodiments which do not utilize an annular extension, the thumb press 300 is configured to nest within the barrel 120.

Figure 13:
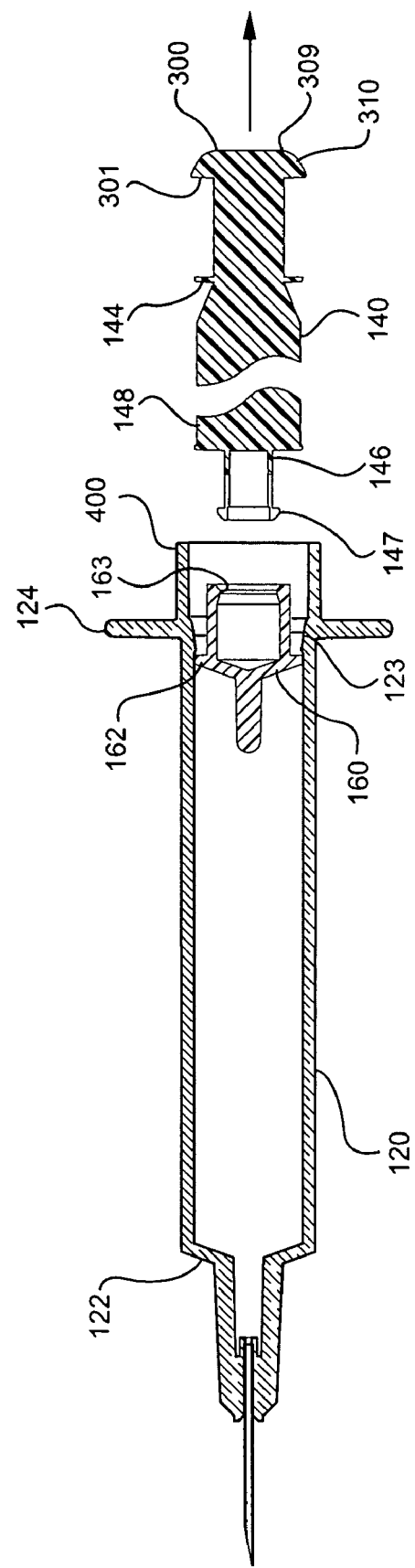
FIG. 13 is an illustration of FIG. 7 showing the plunger rod being moved in the proximal direction and the stopper disengaging from the plunger rod.

FIG. 13 shows the syringe assembly in a configuration in which the stopper 160 has separated from the stopper-engaging portion 146. According to one or more embodiments of the invention, the stopper 160 and stopper-engaging portion 146 disengage to prevent a user from disassembling the parts of the syringe assembly prior to use. As otherwise described in reference to FIG. 5, the peripheral edge 162 of the stopper 160 has a diameter greater than the diameter of the interior surface of the rib 123. Consistent with at least one embodiment of the invention, when a user applies a force to the plunger rod 140 in the proximal direction, the rib 123 locks the peripheral edge 162 of the stopper 160, and the rim 147 of the stopper-engaging portion 146 disconnects from the neck 163 of the stopper. The rib 123 exerts a greater force on the peripheral edge of the stopper than the force or friction exerted by the rim of the stopper-engaging portion of the plunger rod and neck portion of the stopper while proximal force is applied to the plunger rod.

In embodiments of the syringe assembly which do not include a rib 123, the stopper separates from the stopper engaging-portion when a user attempts to pull the plunger rod out of the barrel. In specific embodiments, the rapid withdrawal of the plunger rod creates a vacuum between the distal wall of the barrel and the stopper and permits the stopper to separate from the stopper-engaging portion. In more specific embodiments, the friction between the peripheral edge of the stopper 162 and the interior surface of the barrel 126 is greater than the force or friction connecting the stopper-engaging portion 146 and the stopper 160.

Figure 14:
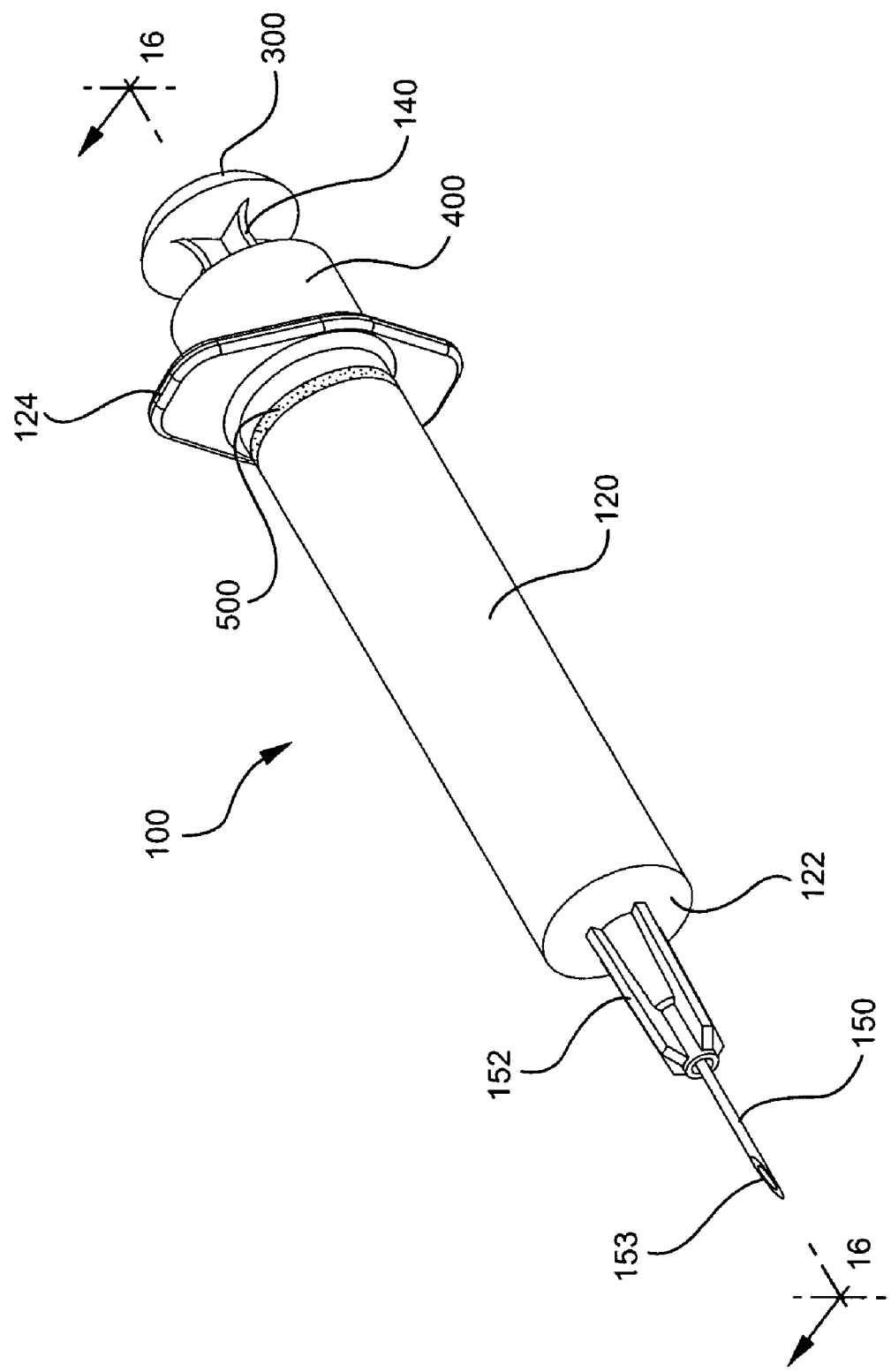
FIG. 14 illustrates a perspective view of an embodiment of a syringe assembly with visual indicators or markers disposed on the barrel and the stopper-engaging portion of the plunger rod.

FIG. 14 shows a syringe assembly 120 in which the barrel includes a visual marker 500. The marker is aligned with the rib 123, as more clearly shown in FIG. 15. The marker can be integrally formed on the sidewall of the barrel or can be added to the exterior surface of the sidewall. The marker can be printed in ink, adhesively applied, a textured surface or a separate piece that is fixed around the syringe barrel. The marker can form a ring around the circumference of the side wall or be in the form of tabs disposed at regular intervals around the circumference of the side wall. In a specific embodiment, the marker is a colored stripe. In a more specific embodiment, the marker can include text in the form of one or more letters and/or numbers, geometric shapes, symbols or combinations thereof to inform users the syringe is disabled.

Figure 15:
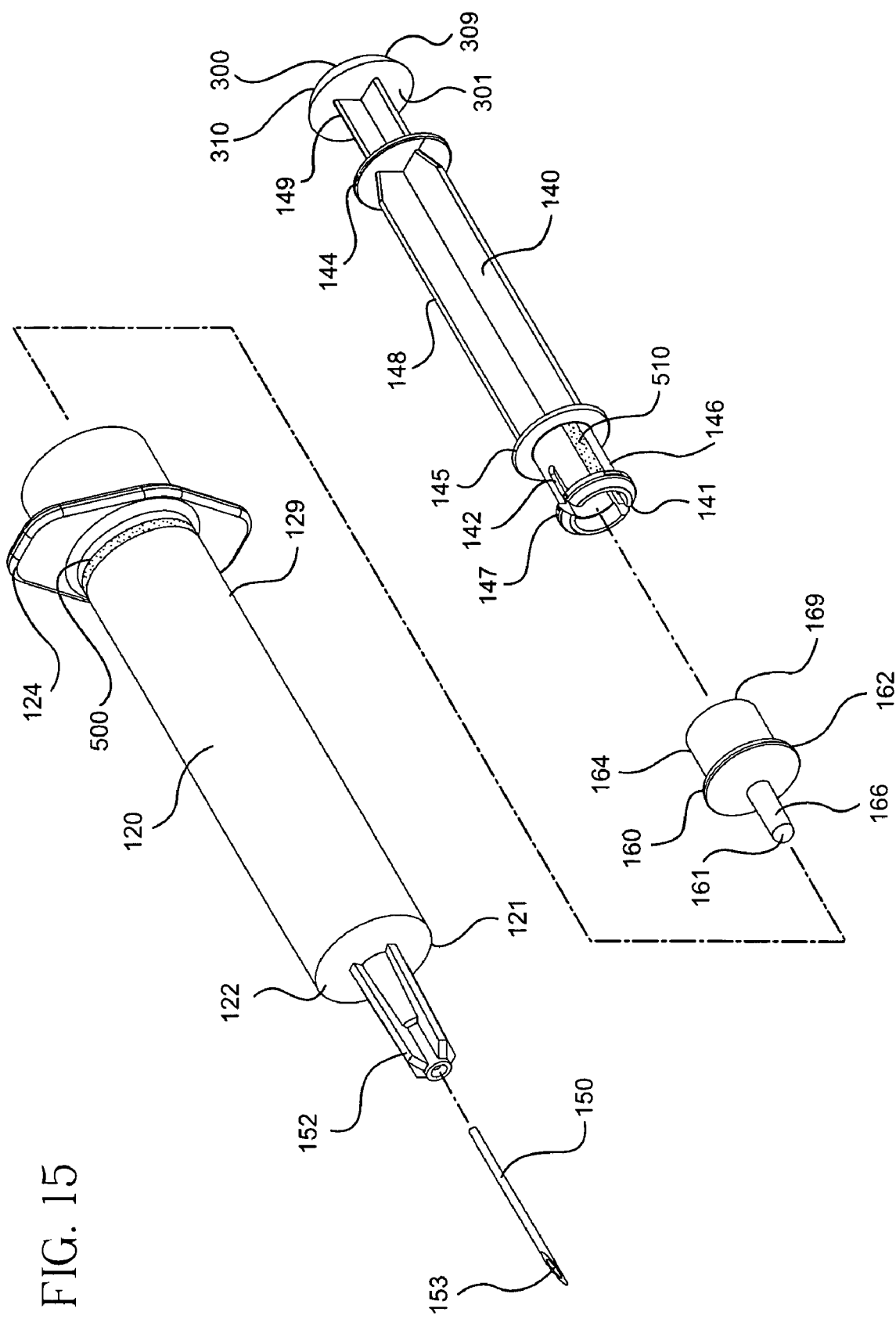
FIG. 15 illustrates a disassembled perspective view of the assembly shown in FIG. 14.

FIG. 15 also shows a plunger rod 140 having a visual indicator or display 510 disposed on the stopper-engaging portion 146. As with the visual marker 500, the visual indicator 510 can be integrally formed with the stopper-engaging portion of the plunger rod or be added to the exterior surface thereof. The indicator or display can be printed in ink, adhesively applied, a textured surface or a separate piece that is fixed to the stopper engaging portion. In one or more embodiments, the indicator or display can comprise a pattern, a solid portion and or can cover the entire surface of the stopper-engaging portion. In a specific embodiment, the indicator is a colored stripe disposed along the length of the stopper-engaging portion 146 between the distal end 141 and the main body 148 of the plunger rod. In a more specific embodiment, the indicator is a colored stripe disposed along the circumference of the stopper-engaging portion 146 of the plunger rod. In an even more specific embodiment, the marker can include text in the form of one or more letters and/or numbers, geometric shapes, symbols or combinations thereof.

As more clearly shown in FIG. 16, a gap between the stopper 160 and the distal end of the main body 148 defines a pre-selected axial distance 132 prior to the injection cycle. The visual indicator 510 is visible when the gap is present. The visual marker 500 is disposed on the exterior surface of the barrel 120 and aligned with the rib 123. As described with reference to FIG. 8, when the user applies a force to the plunger rod 140 in the proximal direction shown by the arrow in FIG. 8, the plunger rod 140 and the stopper 160 move together in the proximal direction, while the stopper-engaging portion 146 is connected to the stopper 160 by the rim 147. In one or more embodiments, the gap defining the pre-selected axial distance 132 is maintained while the stopper 160 and plunger rod 140 move together in the proximal direction along the interior surface of the syringe barrel. Accordingly, the visual indicator 510 continues to be visible.

As described with reference to FIG. 9, when expelling the contents of the syringe, the plunger rod moves in a distal direction the length of the pre-selected axial distance 132 shown in FIGS. 7 and 14 while the stopper body remains stationary, consequently closing the gap defining the pre-selected axial distance 132. The movement of the stopper-engaging portion, in the distal direction relative to the stopper allows the stopper-engaging portion 146 of the plunger rod to move into the recess 168 of the stopper (as shown in FIG. 9). As can be more clearly seen in FIG. 15, this relative movement allows the stopper body 164 to cover the stopper-engaging portion 146 and block visibility of the visual indicator 510.

Figure 18:
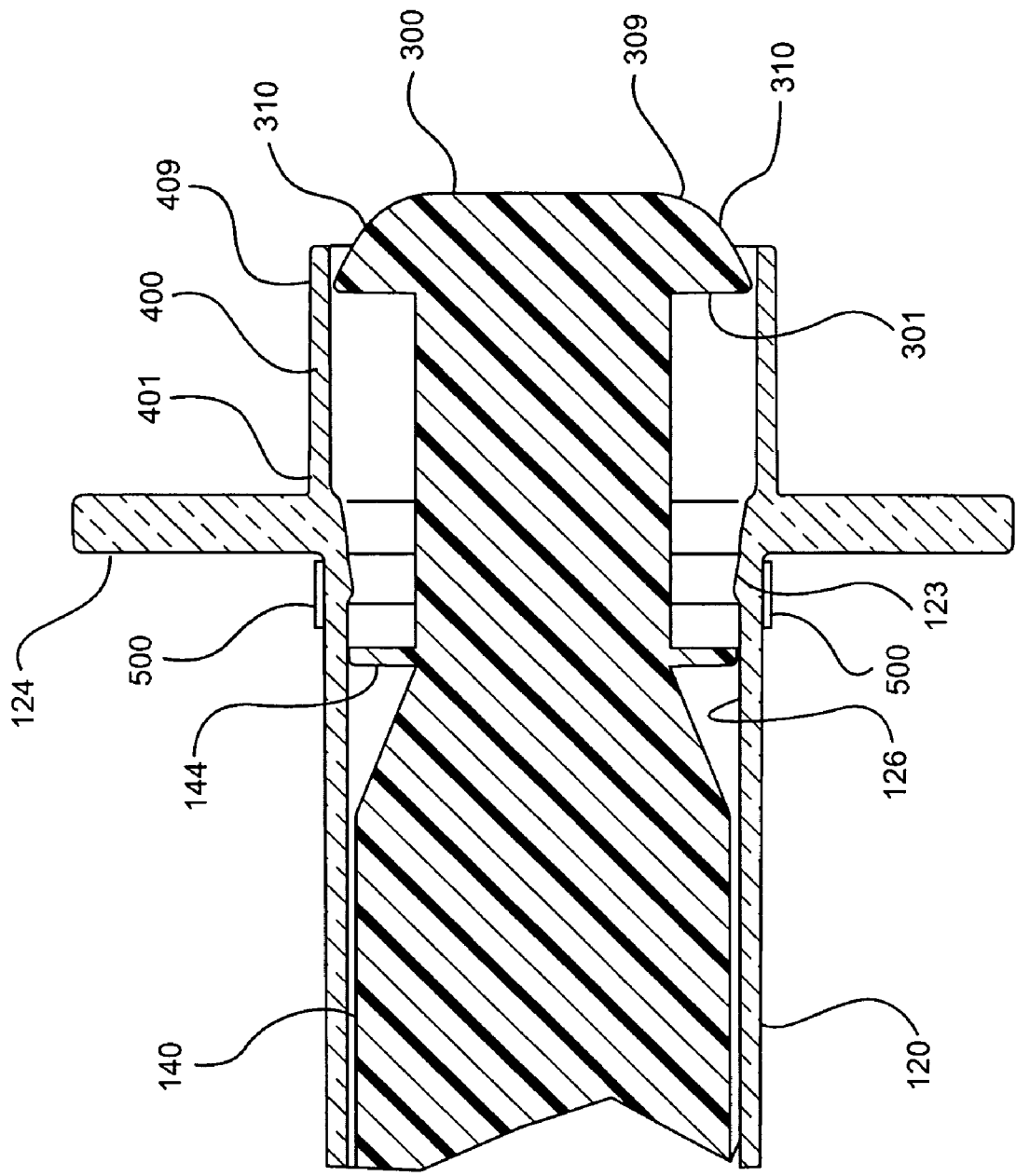
FIG. 18 is an enlarged view of a proximal portion of the assembly shown in FIG. 17.
Figure 19:
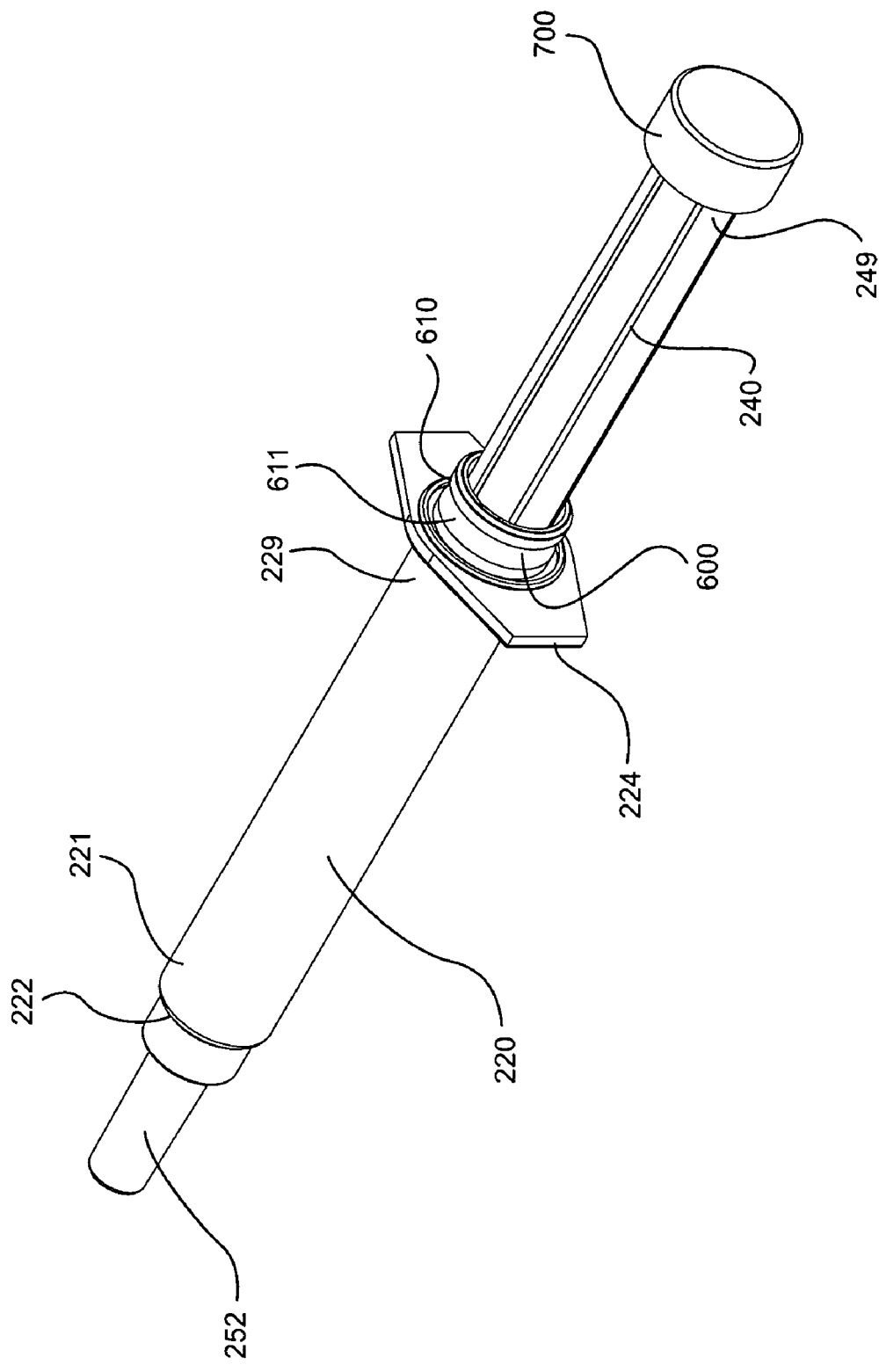
FIG. 19 is perspective view of a syringe assembly according to alternative embodiment of the invention.

As more clearly shown in FIGS. 17 and 18, the visual marker 500 disposed on the barrel 120 and aligned with the rib 123 can also provide visual notice that the syringe assembly is disabled and the advancement of the protrusion 144 past the rib 123. In one or more embodiments, when the stopper-engaging portion enters the recess 168 of the stopper 160 (as also shown in FIG. 9), the gap defining the pre-selected axial distance 132 is closed and the protrusion 144 is permitted to advance past the rib 123 and/or the thumb press 300 is permitted to distally move into the annular extension 400 (as more clearly shown in FIGS. 10 and 11). In such embodiments, the location of the protrusion 144 relative to the visual marker 500 indicates whether the plunger rod has been locked within the barrel and the syringe assembly has been disabled. Before the plunger rod is locked, the protrusion 144 is proximally adjacent to the visual marker 500. Once the plunger rod is locked, the protrusion 144 is distally adjacent to the visual marker 500.

The visual marker 500 can also be used in embodiments of the syringe assembly which do not include a rib or a protrusion. In such embodiments, the visual marker can be at other locations along the length of the barrel to visually notify the user that the syringe is disabled. For example, the visual marker can be disposed near the proximal end of the barrel or on the annular extension so that it is aligned distally adjacent to a corresponding point on the plunger rod. In use, once the distal end of the stopper is in contact with the distal wall of the barrel, the visual marker moves from a distally adjacent location to the corresponding point on the plunger rod to a proximally adjacent to the corresponding point on the plunger rod. The corresponding point can include a corresponding visual marker added to the plunger or an existing feature of a plunger rod such as a tapered portion of the plunger rod body 148 or the contoured portion of the thumb press 310.

It will be appreciated that each of the visual marker 500 and the visual indicator 510 can be used alone or in combination.

FIGS. 19-24 show an embodiment of syringe assembly having an alternative means for preventing removal of the plunger rod from the barrel after the syringe assembly has been used. In the embodiment shown in FIG. 20, the assembly includes a barrel 220, a plunger rod 240 and a stopper 260, arranged so that the proximal end of stopper 269 is attached to the distal end of the plunger rod 241. The stopper 260 then plunger rod 240 is inserted into the proximal end of the barrel 229. A flange 224 is attached at the proximal end 229 of the barrel 220. The barrel 220 further includes an attachment hub 252 at the opening in the distal wall 222 of the barrel 220. One or more embodiments the attachment hub 252 attaches a needle cannula 250 (not shown) to the distal wall 222. The assembly may also include a protective cap over the needle cannula (not shown) or a needle retraction system (not shown).

Figure 22:
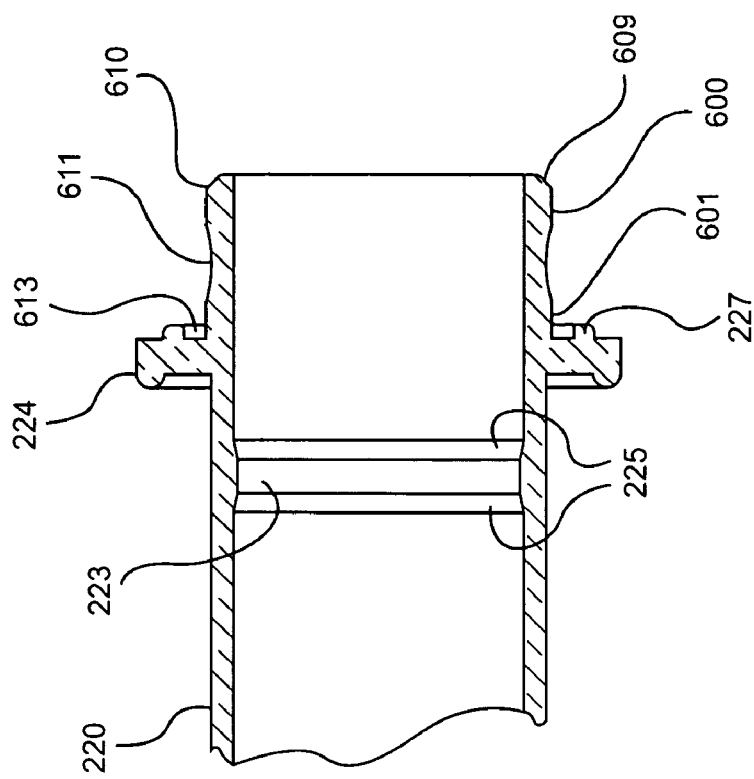
FIG. 22 is an enlarged cross-sectional view taken along line 22-22 of the proximal end of the syringe barrel shown in FIG. 20.

As more clearly shown in FIG. 22, the barrel can further include a locking rib 223, locking rib or other means for preventing removal of the plunger rod from the barrel, having an interior surface with a smaller diameter than the diameter of the interior surface of the barrel. Optional transition diameter regions 225 can also be included to facilitate activation of the means for preventing removal of the plunger rod from the barrel. A collar 600 having a distal end 601 and a proximal end 609 is attached to the proximal end 229 of the barrel and includes an annular member 610 having an indentation 611 and a groove 613 defined by the perimeter 227.

Figure 20:
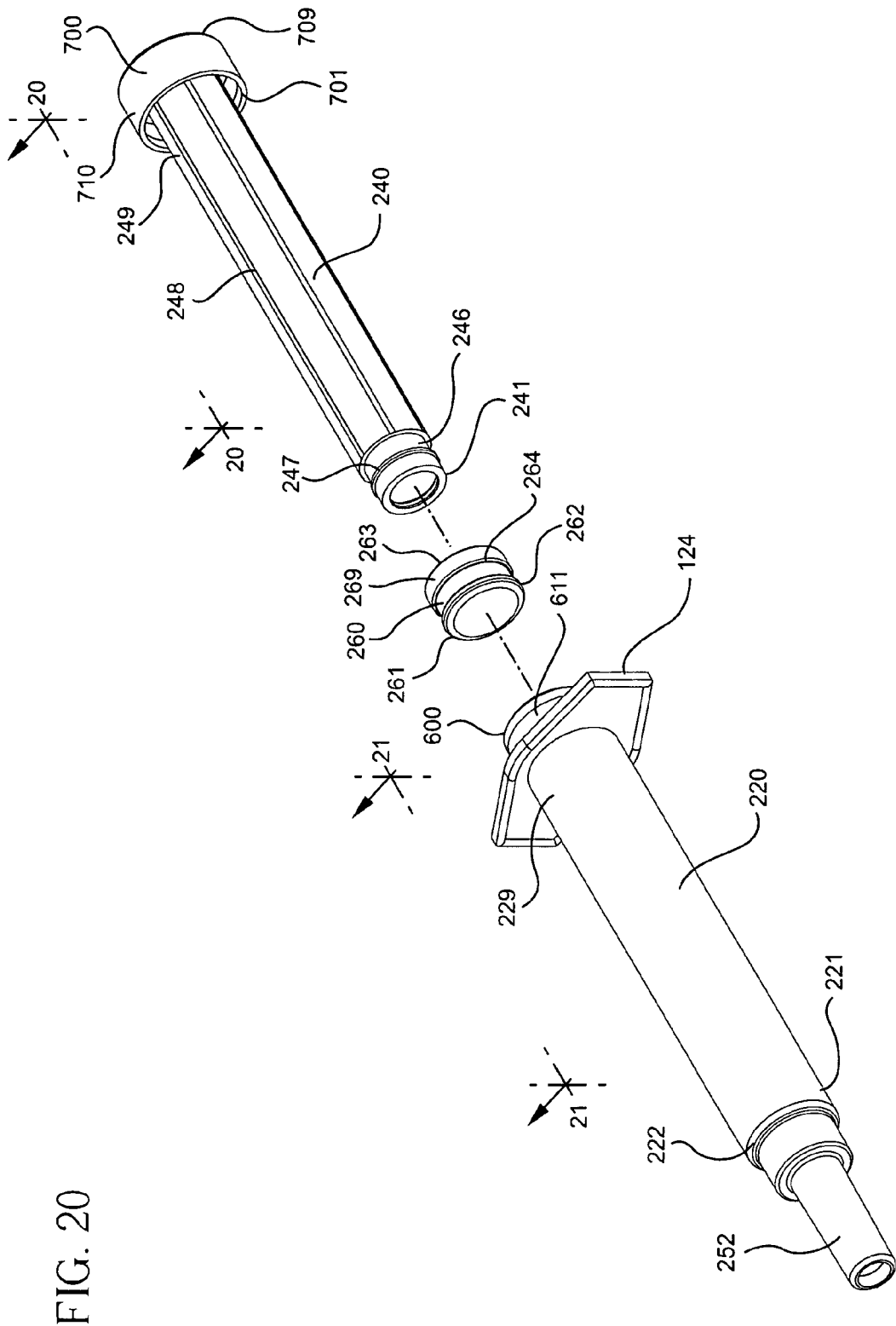
FIG. 20 is a disassembled perspective view of the syringe assembly shown in FIG. 19.
Figure 21:
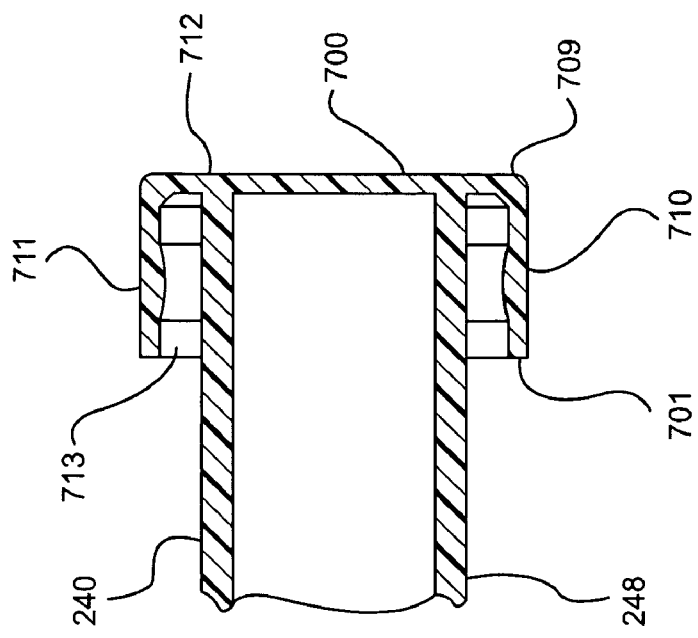
FIG. 21 is a enlarged cross-sectional view taken along line 21-21 of the proximal end of the plunger rod shown in FIG. 20.

Referring now to FIGS. 20 and 21, the plunger rod 240 is shown as having a main body 248, a distal end 241 and a proximal end 249. The plunger rod 240 further includes a thumb press cap 700 at its proximal end 249 and a stopper-engaging portion 246 at its distal end 241 for attaching the stopper 260 to the plunger rod 240. As shown more clearly in FIG. 20, the stopper-engaging portion 246 also includes a plunger recess (not shown) and a retainer 247. At least one embodiment of the invention includes a press-fit attachment or other suitable means for retaining the end of the stopper. The thumb press cap 700 shown in FIGS. 21-23 includes a distal end 701, proximal end 709 including an end wall 712 and a sidewall 710 between the distal end 701 and the proximal end 709 defining a cavity 713 with the main body 248 of the plunger. The side wall 710 further includes a projection 711.

The stopper 260 shown in FIG. 20 includes a distal end 261 having a peripheral edge 262, a proximal end 269 and a peripheral edge 262 which forms a seal with the interior wall of the barrel 220. In embodiments utilizing a locking rib 223, the peripheral edge 262 of the stopper 260 may have a diameter greater than the diameter of the interior surface of the barrel at the location of the rib 223 and thereby provides a means for separating the stopper from the stopper-engaging portion. The stopper 260 can further include a stopper body 264 having a peripheral lip 263 at its proximal end 269 that forms a recess (not shown). The peripheral edge 262 of the stopper 260 forms a seal with the interior surface of the barrel 220. The retainer 247 of the stopper-engaging portion 246 retains the peripheral lip 263 of the stopper 260 to connect the stopper 260 to the plunger rod 240.

As with the syringe assemblies shown in FIGS. 7-10, a gap between the stopper 260 and the distal end of the main body 248 defines a pre-selected axial distance (not shown). The distance between the peripheral edge 262 and the end wall 712 of the thumb press cap 700 defines a first length L1 (not shown). As described with reference to FIGS. 7-10, as the pre-selected axial distance is reduced by the relative movement between the stopper 260 and the stopper-engaging portion 246 during the aspiration and injection cycles of the syringe assembly, the distance between the peripheral edge 262 of the stopper 260 and the thumb press cap 700 is reduced to a second length L2 (not shown). In one embodiment, the user may inject a limited amount of the fluid aspirated or exert a limited force on the plunger rod in the distal direction to flush or expel some of the aspirated fluid, without locking the plunger rod, provided that the syringe assembly is not bottomed. However, as will be described further below, a user will typically expel substantially all of the contents of the syringe by bottoming the stopper on the distal wall of the barrel.

Figure 23:
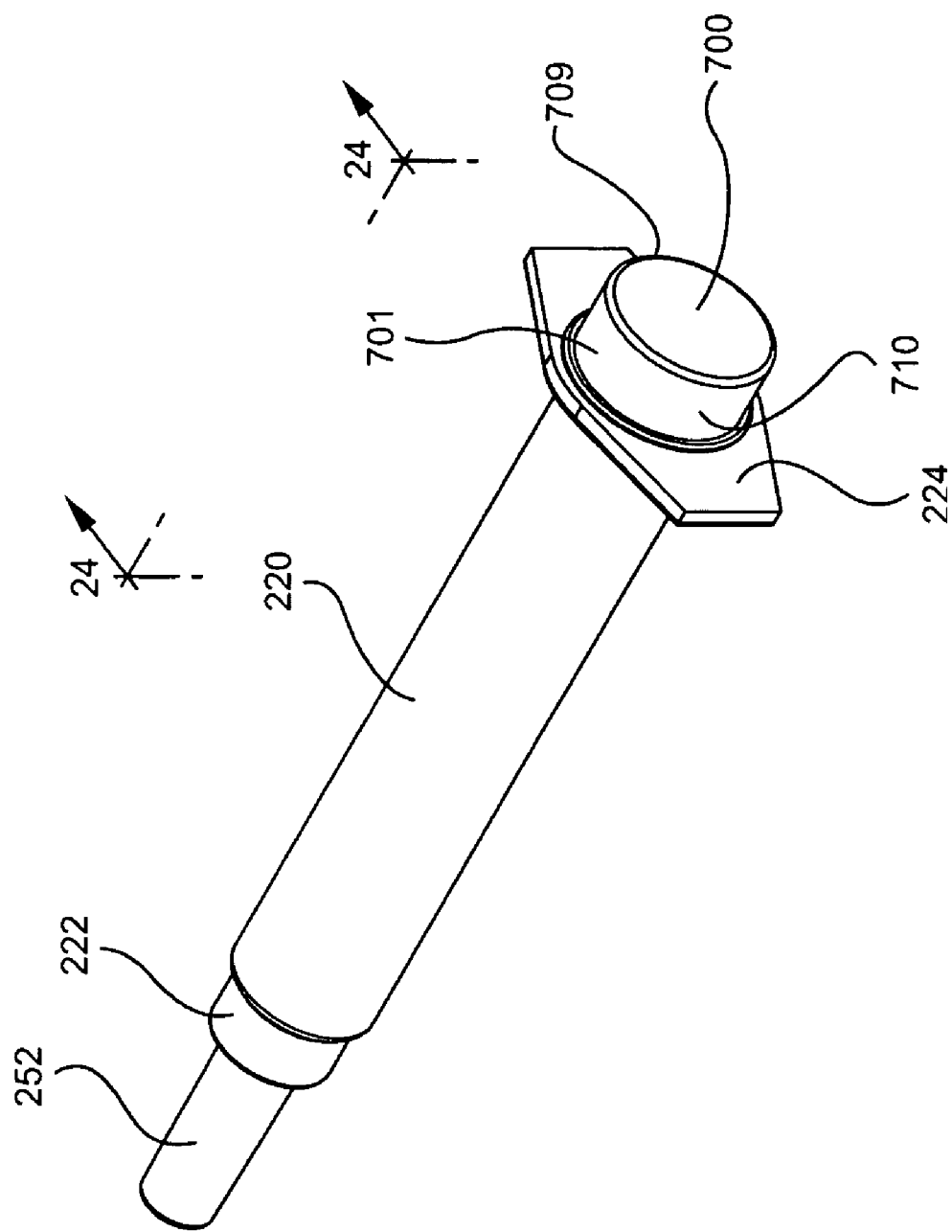
FIG. 23 is an illustration of FIG. 19 showing the thumb press locked to the syringe barrel.
Figure 24:
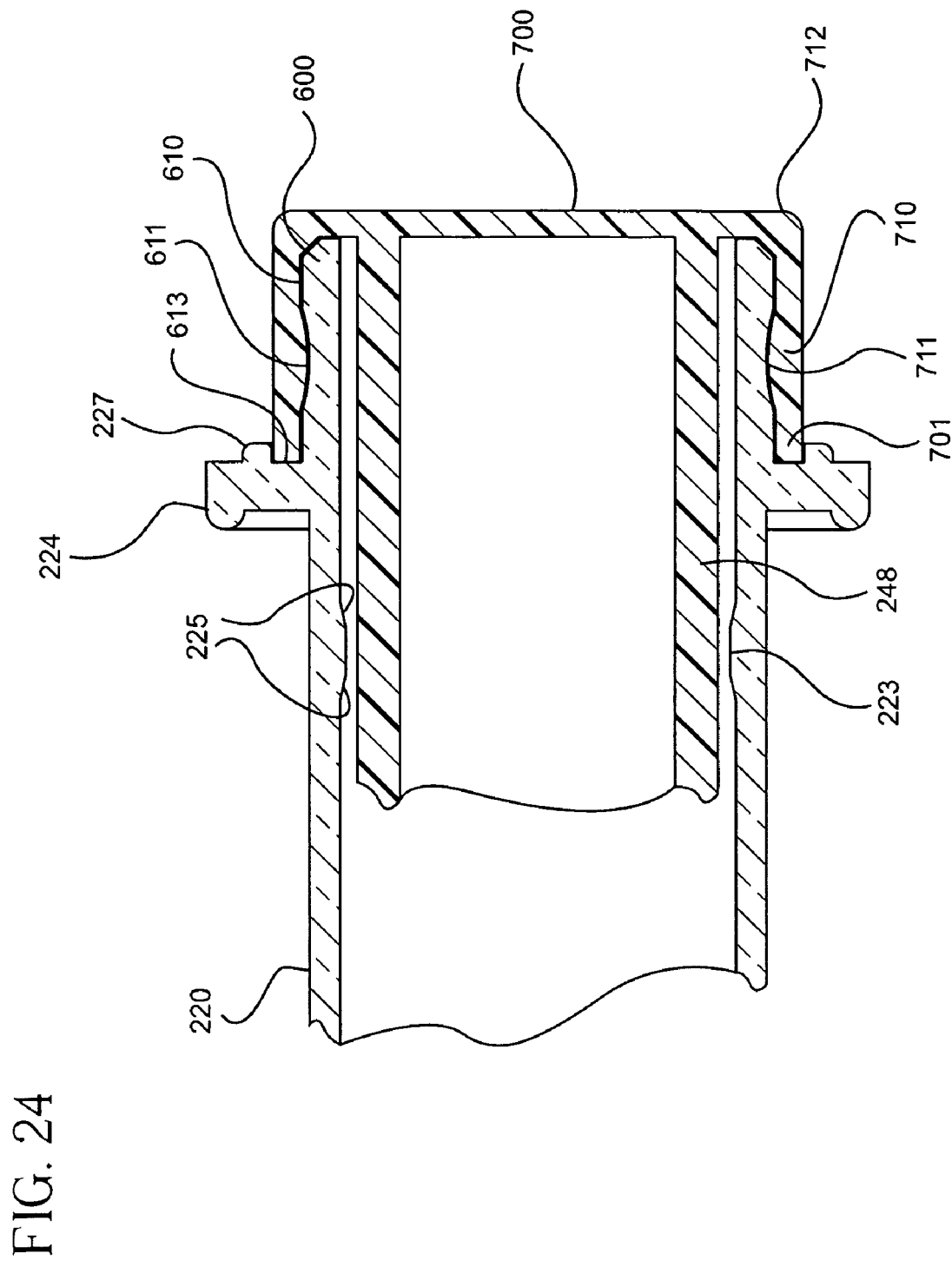
FIG. 24 is an enlarged cross-sectional view taken along line 24-24 of the proximal end of the syringe assembly shown in FIG. 23.

FIGS. 23-24 which illustrates the syringe assembly after the reduced length L2 permits the thumb press cap 700 to advance distally into the collar 600 in a nested configuration with the collar. The annular member 610 of the collar 600 nests within cavity 713 of the thumb press cap 700. The side wall 710 of the thumb press cap 700 nests within the groove 613 of the collar 600. As more clearly shown in FIG. 23, the projection 711 and the indentation 611 align to lock the thumb press cap 700 to the collar 600 at the proximal end of the barrel 229.

It will be appreciated, as previously described, that the stopper and plunger rod can be connected in a fixed relationship such that the distal movement of the stopper and plunger rod permits the thumb press can to advance distally into the collar in a nested configuration with the collar.

In one or more embodiments, the plunger rod 240 may include a protrusion as described with reference to FIGS. 1-18 which is permitted to advance distally past the locking rib 223 of the embodiment shown in FIG. 22 to prevent removal of the plunger rod from the barrel. The protrusion as described with reference to FIGS. 1-18 may be used in conjunction with the thumb press cap 700 and the collar 600 of the embodiments of FIGS. 19-24. It will also be understood that the protrusion 144, annular extension 400, thumb press 300 having a contoured portion 310 and the thumb press cap 700 and collar 600 can be used alone or in various combinations to prevent removal of the plunger rod or reuse of the syringe assembly.

Embodiments of the syringe assembly of FIGS. 19-24 can also include a visual marker, visual indicator or both, as described with reference to FIGS. 14-18. In a specific embodiment, the barrel may include a visual marker that indicates the syringe assembly has been disabled. In a more specific embodiment, the barrel 220 of one or more embodiments can also include a visual marker aligned with the locking rib 223. In a more specific embodiment, the syringe assembly can include a visual indicator disposed on the stopper engaging portion 246.

According to one or more embodiments, the syringe barrel may include identifying information on the syringe assembly. Such information can include, but is not limited to one or more of identifying information regarding the contents of the syringe assembly or information regarding the intended recipient.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A syringe assembly comprising:
   a barrel including a cylindrical sidewall having an interior surface defining a chamber for retaining fluid, an open proximal end and a distal end including a distal wall having an opening therethrough in fluid communication with said chamber;
   an elongate plunger rod including a proximal end, a distal end, and a main body extending between the proximal and distal end, the plunger rod being distally and proximally movable within said chamber, the proximal end including a thumb press having proximal end, a distal end, and a diameter, the distal end of the plunger rod including a stopper-engaging portion;
   an annular extension protruding proximally from the proximal end of the barrel having a diameter greater than the diameter of the thumb press; and
   a stopper having a proximal end and a distal end, the stopper attached to the stopper-engaging portion of the plunger rod and distally and proximally movable relative to the stopper-engaging portion for a pre-selected axial distance, such that when the distal end of the stopper is in contact with the distal wall of the barrel, the thumb press is permitted to advance distally into the annular extension and the annular extension at least partially envelopes a portion of the thumb press to prevent the user from accessing the thumb press and moving the plunger rod in a proximal direction, the stopper-engaging portion comprising a visual indicator being fully visible when the stopper-engaging portion is proximally moved relative to the stopper.

2. The syringe assembly of claim 1, wherein the annular extension fully envelopes the length of the thumb press.

3. The syringe assembly of claim 1, wherein the diameter of the thumb press decreases from the distal end of the thumb press to the proximal end of the thumb press.

4. The syringe assembly of claim 1, wherein the annular extension further comprises a detent and the thumb press further comprises a retaining ring, the detent configured to engage the retaining ring to lock the thumb press at the proximal end of the barrel when the distal end of the thumb press is permitted to advance distally into the annular extension.

5. The syringe assembly of claim 1, wherein the barrel further comprises a rib adjacent said proximal end and a diameter transition region having an axial length extending from the rib towards said proximal end such that the diameter of the barrel increases along the transition region from the rib towards the proximal end.

6. The syringe assembly of claim 5, wherein the plunger rod further comprises a protrusion between the thumb press and the main body, the protrusion having a diameter greater than the diameter of the barrel at the rib such that when the distal end of the stopper is in contact with the distal wall of the barrel, the protrusion is permitted to advance distally past the rib in the barrel and lock the plunger rod in the barrel to prevent reuse of the syringe assembly.

7. The syringe assembly of claim 6, wherein the protrusion is tapered to facilitate distal movement.

8. The syringe assembly of claim 1, wherein the application of an initial proximally directed force to the plunger rod, while holding the barrel, causes the plunger rod to move the length of the axial distance in a proximal direction within the barrel, while the stopper remains stationary.

9. The syringe assembly of claim 8, wherein the stopper-engaging portion of the plunger rod is connected to the stopper where in the application of a continuous proximally directed force to the plunger rod, while holding the barrel, causes the stopper and the plunger rod to move together in a proximal direction within the barrel.

10. The syringe assembly of claim 9, wherein the stopper-engaging portion of the plunger rod is connected to the stopper where in the application of an initial distally directed force to the plunger rod after application of a proximally directed force to the plunger rod, while holding the barrel, causes the stopper to remain stationary and the plunger to move the length of the axial distance in the distal direction within the barrel.

11. The syringe assembly of claim 10, wherein the stopper-engaging portion of the plunger rod is connected to the stopper where in the application of a continuous distally directed force to the plunger rod causes the stopper and plunger rod to move together in the distal direction within the barrel until the stopper reaches the distal end of the barrel.

12. The syringe assembly of claim 1, wherein the visual indicator is not visible when the stopper-engaging portion is distally moved relative to stopper.

13. The syringe assembly of claim 1, further comprising a visual marker disposed on the barrel.

14. The syringe assembly of claim 6, further comprising a visual marker disposed on the barrel.

15. The syringe assembly of claim 1, wherein the stopper further comprises a stopper boss at the proximal end of the stopper, a frangible connection connecting said stopper to the plunger rod and a peripheral lip at a proximal end of the stopper boss.

16. The syringe assembly of claim 1, wherein application of a continuous proximally directed force on the plunger rod causes the stopper-engaging portion to disengage from the stopper.

17. The syringe assembly of claim 1, wherein the proximal end of the barrel further comprising a flange and the annular extension protrudes in a proximal direction beyond the flange.

18. A syringe assembly comprising:
   a barrel including a cylindrical sidewall having an interior surface defining a chamber for retaining fluid, an open proximal end and a distal end including a distal wall having an opening therethrough in fluid communication with said chamber, the chamber further having a first inner diameter;
   an elongate plunger rod having a proximal end, a distal end, a stopper-engaging portion located at the distal end of the plunger rod, a thumb press having a proximal end, a distal end, a diameter and a length at the proximal end of the plunger rod, a main body portion extending between the distal and proximal ends of the plunger rod;
   an annular extension protruding proximally from the proximal end of the barrel configured to form a nestable arrangement with at least a portion of the length of the thumb press at the distal end of the thumb press; and
   a stopper having a proximal end and a distal end, the stopper attached to the stopper-engaging portion of the plunger rod and distally and proximally movable relative to the stopper-engaging portion such that when the distal end of the stopper is in contact with the distal wall of the barrel, the thumb press is permitted to advance distally and nestably engage with the annular extension to prevent the user from engaging the thumb press to move the plunger rod in a proximal direction, the stopper-engaging portion comprising a visual indicator being fully visible when the stopper-engaging portion is proximally moved relative to the stopper.

19. The syringe assembly of claim 18, wherein the annular extension provides a nesting area for the thumb press and a flange at the proximal end of the barrel, wherein the annular extension protrudes in a proximal direction beyond the flange.

20. The syringe assembly of claim 18, wherein the diameter of the thumb press decreases from the distal end of the thumb press to the proximal end of the thumb press.

21. The syringe assembly of claim 18, wherein the thumb-press further comprises a retaining ring and the annular extension further comprises a detent and is configured to engage the retaining ring when the thumb press is permitted to advance distally and the annular extension forms a nested arrangement with the thumb press to lock the thumb press at the proximal end of the barrel.

22. The syringe assembly of claim 18, wherein the barrel further comprises a locking rib adjacent to the open proximal end having a second inner diameter, wherein the second inner diameter is less than the first inner diameter, an increased diameter region located proximally from the locking rib having a third inner diameter greater than the second inner diameters, and a diameter transition region extending between the locking rib and the increased diameter region.

23. The syringe assembly of claim 22, wherein the plunger rod further comprises a protrusion extending radially from the plunger rod having an outer diameter greater than the second inner diameter such that when the distal end of the stopper is in contact with the distal wall of the barrel, the protrusion is permitted to advance distally past the locking rib in the barrel and lock the plunger rod in the barrel to prevent reuse of the syringe assembly.

24. The syringe assembly of claim 23, wherein the protrusion is tapered to facilitate distal movement past the locking rib.

25. The syringe assembly of claim 18, wherein the application of an initial proximally directed force to the plunger rod while holding the barrel, causes the plunger rod to move the length of an axial distance in a proximal direction within the barrel, while the stopper remains stationary.

26. The syringe assembly of claim 25, wherein the stopper-engaging portion of the plunger rod is connected to the stopper such that application of a continuous proximally directed force to the plunger rod, while holding the barrel, causes the stopper and the plunger rod to move together in a proximal direction within the barrel and applying an initial distally directed force to the plunger rod after application of a proximally directed force to the plunger rod, while holding the barrel, causes the stopper to remain stationary and the plunger to move the length of the axial distance in the distal direction within the barrel.

27. The syringe assembly of claim 26, wherein the stopper-engaging portion of the plunger rod is connected to the stopper such that application of a continuous distally directed force to the plunger rod causes the stopper and plunger rod to move together in the distal direction within the barrel until the stopper reaches the distal end of the barrel.

28. The syringe assembly of claim 22, wherein the stopper has a diameter greater than the second inner diameter and, upon application of a continuous proximally directed force on the plunger rod, the locking rib prevents proximal movement of the stopper and causes the stopper-engaging portion to detach from the stopper.

29. The syringe assembly of claim 28, wherein the stopper further comprises a stopper boss at the proximal end of the stopper, a frangible connection connecting said stopper to the plunger rod and a peripheral lip at a proximal end of the stopper boss.

30. The syringe assembly of claim 29, wherein the stopper-engaging portion of the plunger rod further comprises a retainer to retain the peripheral lip of the stopper.

31. The syringe assembly of claim 29, wherein the stopper has a diameter greater than the second inner diameter and, upon application of a continuous proximally directed force on the plunger rod, the locking rib prevents proximal movement of the stopper and causes the frangible connection to break.

32. The syringe assembly of claim 18, wherein the visual indicator is not visible when the stopper-engaging portion is moved distally relative to the stopper.

33. The syringe assembly of claim 18, further comprising a visual marker disposed on the barrel and aligned with a visual alignment marker disposed on the plunger rod so that when the distal end of the stopper is in contact with the distal wall of the barrel, the position of the visual alignment marker moves from being positioned proximally adjacent to the visual marker to distally adjacent to the visual marker to indicate the plunger rod is locked in the barrel.

34. The syringe assembly of claim 18, wherein the proximal end of the barrel further comprises a flange and the annular extension protrudes in a proximal direction beyond the flange.

35. A syringe assembly comprising:
a barrel including a cylindrical sidewall having an interior surface defining a chamber for retaining fluid, an open proximal end and a distal end including a distal wall having an opening therethrough in fluid communication with said chamber;
an elongate plunger rod having a proximal end, a distal end, a stopper-engaging portion located at the distal end of the plunger rod, a thumb press at the proximal end of the plunger rod, and a main body portion extending between the distal and proximal ends of the plunger rod;
a stopper having a proximal end and a distal end, the stopper attached to the stopper-engaging portion of the plunger rod and distally and proximally movable relative to the stopper-engaging portion, the stopper-engaging portion comprising a visual indicator being fully visible when the stopper-engaging portion is proximally moved relative to the stopper,
means for preventing removal of the plunger rod from the barrel to prevent reuse of the syringe assembly when the distal end of the stopper is in contact with the distal wall of the barrel and distal force is applied to the thumb press; and
means for separating stopper from the stopper-engaging portion upon application of sufficient proximal force to the plunger rod.

36. The syringe assembly of claim 35, wherein the means for preventing removal of the plunger rod from the barrel comprises a nestable thumb press disposed at the proximal end of the plunger rod configured to advance into the chamber of the barrel in a nested configuration with the barrel.

37. The syringe assembly of claim 35, wherein the means for preventing removal of the plunger rod from the barrel comprises a collar for locking the thumb press at the proximal end of the barrel.

38. The syringe assembly of claim 35, further comprising means indicating the stopper is in contact with the distal wall of the barrel and distal force is has been applied to the thumb press.

* * * * *